(12) United States Patent
Fan et al.

(10) Patent No.: US 9,216,030 B2
(45) Date of Patent: Dec. 22, 2015

(54) LAPAROSCOPIC FORCEPS ASSEMBLY

(71) Applicant: GYRUS ACMI, INC., Southborough, MA (US)

(72) Inventors: Tailin Fan, Nashua, NH (US); Kester Batchelor, Mound, MN (US); John R. Mensch, Plymouth, MN (US); Richard A. Thompson, St. Louis Park, MN (US)

(73) Assignee: GYRUS ACMI, INC., Southborough, MA (US)

( * ) Notice: Subject to any disclaimer, the term of this patent is extended or adjusted under 35 U.S.C. 154(b) by 0 days.

(21) Appl. No.: 14/484,341

(22) Filed: Sep. 12, 2014

(65) Prior Publication Data

US 2015/0105820 A1    Apr. 16, 2015

Related U.S. Application Data

(60) Provisional application No. 61/889,060, filed on Oct. 10, 2013.

(51) Int. Cl.
*A61B 17/00* (2006.01)
*A61B 17/29* (2006.01)
(Continued)

(52) U.S. Cl.
CPC .............. *A61B 17/29* (2013.01); *A61B 17/295* (2013.01); *A61B 18/1445* (2013.01);
(Continued)

(58) Field of Classification Search
CPC ........... A61B 18/1445; A61B 18/1442; A61B 18/1402; A61B 17/2812; A61B 17/285; A61B 2018/1452; A61B 2018/1455; A61B 2017/2932; A61B 2017/2933; A61B 2017/2934; A61B 2017/2936; A61B 17/29; A61B 17/295; A61B 18/1447; A61B 2017/2944; A61B 2017/2902; A61B 2017/2926; A61B 2018/1457
See application file for complete search history.

(56) References Cited

U.S. PATENT DOCUMENTS

| 3,934,589 A | 1/1976 | Zimmer |
| 3,967,625 A | 7/1976 | Yoon |

(Continued)

FOREIGN PATENT DOCUMENTS

| EP | 2578174 A1 | 4/2013 |
| EP | 2594211 A1 | 5/2013 |
| WO | WO 95/07662 A1 | 3/1995 |

OTHER PUBLICATIONS

Halo PKS Cutting Forceps, available at www.olympus-osta/halo.html, last accessed on Apr. 3, 2014.

(Continued)

*Primary Examiner* — Ashley Fishback
(74) *Attorney, Agent, or Firm* — The Dobrusin Law Firm, P.C.

(57) ABSTRACT

A laparoscopic forceps comprising a handpiece including a distal end portion; a tubular member protruding from the distal end portion of the handpiece, the tubular member having a distal end with a distal opening, a pair of jaws having legs that are disposed within the tubular member and partially protruding from the distal opening, the jaws and the tubular member being movable relative to each other; wherein each of the jaws has an arcuate section; an operable mechanism for creating relative motion between the jaws and the tubular member along a direction parallel to the longitudinal axis, and one or more spacing members extending across the distal opening of the tubular member and between the jaws; wherein the jaws are closable by the relative movement of the tubular member and the jaws towards each other so that the tubular member advances over the arcuate section of the jaws, and the jaws are openable by the relative movement of the tubular member and the jaws away from each other so that the one or more spacing members extend between the jaws and the jaws are moved apart.

19 Claims, 20 Drawing Sheets

(51) Int. Cl.
*A61B 17/295* (2006.01)
*A61B 18/14* (2006.01)

(52) U.S. Cl.
CPC .... *A61B 18/1447* (2013.01); *A61B 2017/2902* (2013.01); *A61B 2017/2926* (2013.01); *A61B 2017/2932* (2013.01); *A61B 2017/2933* (2013.01); *A61B 2017/2934* (2013.01); *A61B 2017/2937* (2013.01); *A61B 2017/2944* (2013.01); *A61B 2018/1455* (2013.01); *A61B 2018/1457* (2013.01)

(56) References Cited

U.S. PATENT DOCUMENTS

| | | |
|---|---|---|
| 4,003,380 A | 1/1977 | Wien |
| 4,016,881 A | 4/1977 | Rioux et al. |
| 4,418,692 A | 12/1983 | Guay |
| 4,427,014 A | 1/1984 | Bel et al. |
| 5,258,006 A | 11/1993 | Rydell et al. |
| 5,318,589 A | 6/1994 | Lichtman |
| 5,425,743 A | 6/1995 | Nicholas |
| 5,445,638 A | 8/1995 | Rydell et al. |
| 5,458,598 A | 10/1995 | Feinberg et al. |
| 5,462,546 A | 10/1995 | Rydell |
| 5,483,952 A | 1/1996 | Aranyi |
| 5,601,572 A | 2/1997 | Middleman |
| 5,611,813 A | 3/1997 | Lichtman |
| 5,620,459 A | 4/1997 | Lichtman |
| 5,647,871 A | 7/1997 | Levine et al. |
| 5,735,849 A | 4/1998 | Baden et al. |
| 5,766,166 A | 6/1998 | Hooven |
| 5,810,805 A | 9/1998 | Sutcu et al. |
| 6,010,523 A | 1/2000 | Sabin |
| 6,113,596 A | 9/2000 | Hooven et al. |
| 6,190,386 B1 | 2/2001 | Rydell |
| 6,270,497 B1 | 8/2001 | Sekino et al. |
| 6,358,268 B1 | 3/2002 | Hunt et al. |
| 6,679,882 B1 | 1/2004 | Kornerup |
| 6,802,843 B2 | 10/2004 | Truckai et al. |
| 7,150,749 B2 | 12/2006 | Dycus et al. |
| 7,377,902 B2 | 5/2008 | Burbank et al. |
| 8,328,802 B2 | 12/2012 | Deville et al. |
| 8,348,967 B2 | 1/2013 | Stulen |
| 8,409,197 B2 | 4/2013 | Staler |
| 8,425,511 B2 | 4/2013 | Olson |
| 8,460,275 B2 | 6/2013 | Taylor et al. |
| 8,496,674 B2 | 7/2013 | Cabrera et al. |
| 8,523,898 B2 | 9/2013 | Bucciaglia et al. |
| 8,535,312 B2 | 9/2013 | Horner |
| 2002/0120266 A1 | 8/2002 | Truckai et al. |
| 2003/0229344 A1 | 12/2003 | Dycus et al. |
| 2006/0084973 A1 | 4/2006 | Hushka |
| 2011/0054462 A1 | 3/2011 | Ellman |
| 2011/0251613 A1 | 10/2011 | Guerra et al. |
| 2012/0253344 A1 | 10/2012 | Dumbauld et al. |
| 2013/0131651 A1 | 5/2013 | Strobl et al. |
| 2013/0190759 A1 | 7/2013 | Waaler et al. |
| 2014/0025071 A1* | 1/2014 | Sims et al. ............ 606/46 |

OTHER PUBLICATIONS

International Search Report, International Application No. PCT/US2014/055311, mailed Dec. 4, 2014.
US 8,419,756, 04/2013, Stulen et al. (withdrawn)

* cited by examiner

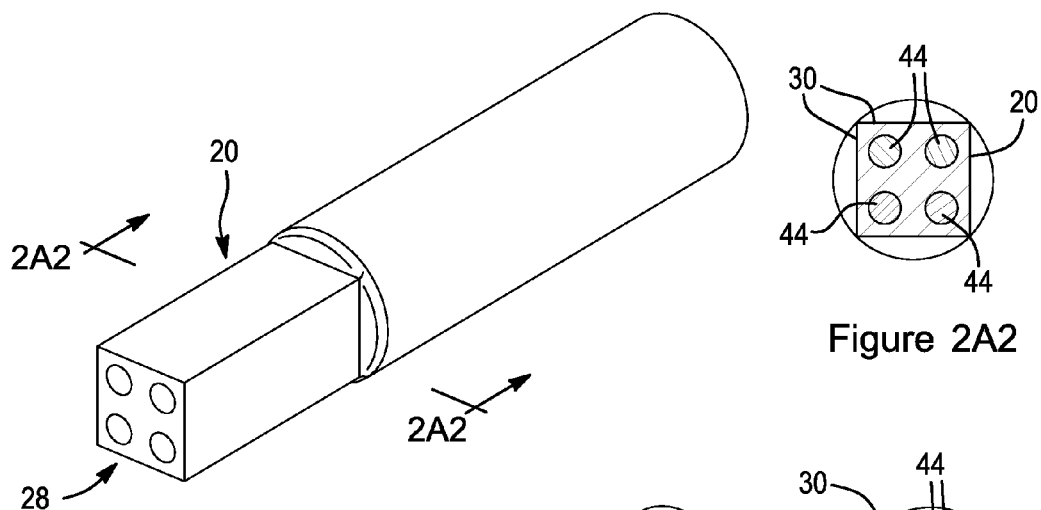
Figure 2A1
Figure 2A2
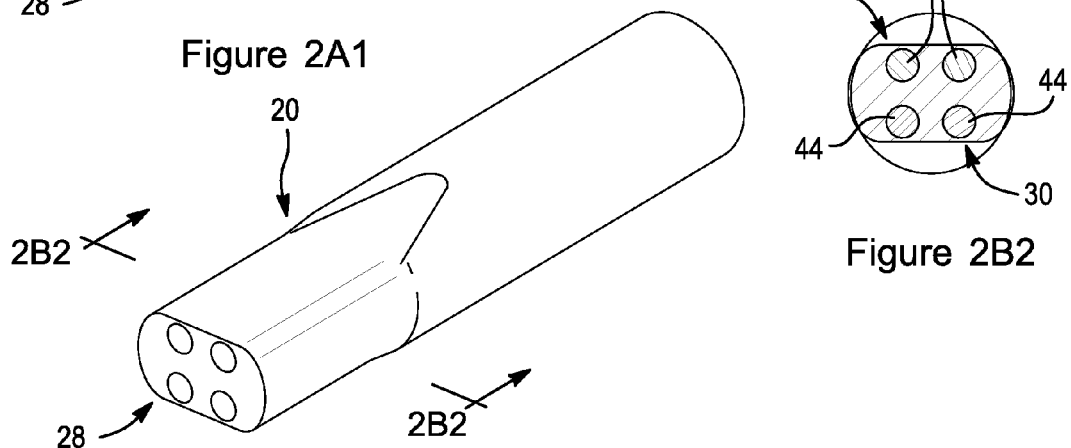
Figure 2B1
Figure 2B2
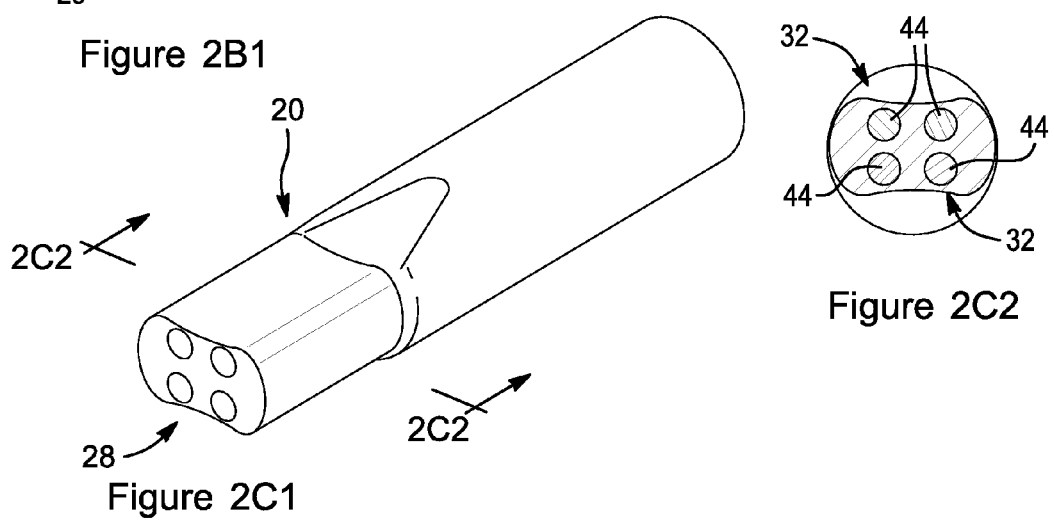
Figure 2C1
Figure 2C2

LAPAROSCOPIC FORCEPS ASSEMBLY

FIELD

The disclosure relates to forceps with a spacing member between two opposing jaws, a tubing member with a non-circular profile, or both.

BACKGROUND

Generally forceps may be utilized for laparoscopic surgery. The forceps may be used to control delicate movements inside a patient. These forceps may be used to grip an anatomical feature. The forceps may include a gripping assembly or a cutting assembly. The forceps may include electrical energy for use in the gripping assembly. The forceps have a pair of opposed resilient jaws that are closed against each other by pulling the jaws into a distal end of a shaft that captures a portion of the jaws that is wider than the distal end opening of the shaft so that the jaws are moved together. Similarly the shaft may be pushed over the jaws so that the jaws are moved together to create a gripping force. In both of these the shaft captures the jaws and acts as a cam that forces the jaws together to create the gripping force. Examples of some forceps with resilient jaws closed by a camming action may be found in U.S. Pat. Nos. 5,458,598; 5,735,849; 5,445,638; 6,190,386; 6,113,596; and 6,679.882 and HALO cutting forceps, available at http://www.olympus-osta.com/halo.htm last accessed on Apr. 3, 2014 all of which are incorporated by reference herein in their entirety for all purposes.

Some laparoscopic forceps include jaws that have two legs that are connected at a distal end forming a gap between the two legs so that a blade can travel down the gap in center of the two opposing jaws. During the camming of the jaws, the jaws may be moved into contact with the blade creating a drag force which may prevent the blade from moving and/or may cause misalignment of the blade. Further, the camming force on the opposing jaws may not be equal and the uneven application of forces on the opposing jaws may cause the distal ends of the jaws to be misaligned during gripping.

The laparoscopic forceps after the jaws are released and the jaws are no longer constrained by the shaft typically move apart. This opening force may be used to push apart tissue by extending the closed jaws proximate to tissue and then allowing the jaws to open so that tissue is moved. However, some of the laparoscopic forceps when released from a closed position do not have a sufficient amount of force to move tissue for dissection. Other active dissection tools allow the user to open and close the jaws through mechanical linkages. These mechanical linkages generally allow the user some control over the amount of force applied to the tissue. However, the mechanical linkages include multiple delicate parts that are difficult to assemble, are expensive, and results in a complex device to move tissue.

It would be attractive for the forceps to include a device that controls the movement between the two opposing jaws. What is needed is a device that assists in biasing the jaws and maintains alignment of the blade. What is needed is a device that opens the jaws. It would be attractive to have a device that spreads the jaws with sufficient force so that the jaws can be used for dissection. What is needed is a device that spreads the jaws and does not interfere with a reciprocating blade.

SUMMARY

The disclosure meets one or more of the needs by providing: a laparoscopic forceps comprising a handpiece including a distal end portion; a tubular member protruding from the distal end portion of the handpiece, the tubular member having a distal end with a distal opening, a pair of jaws having legs that are disposed within the tubular member and partially protruding from the distal opening in the distal end of the tubular member, the pair of jaws and the tubular member being movable relative to each other in a direction parallel to a longitudinal axis of the tubular member; wherein each of the pair of jaws has an arcuate section; an operable mechanism for creating relative motion between the pair of jaws and the tubular member along a direction parallel to the longitudinal axis of the tubular member, and one or more spacing members extending across the distal opening of the tubular member and between the pair of jaws; wherein the pair of jaws are closable by the relative movement of the tubular member and the pair of jaws towards each other so that the tubular member advances over the arcuate section of the pair of jaws, and the pair of jaws are openable by the relative movement of the tubular member and the pair of jaws away from each other so that the one or more spacing members extend between the pair of jaws so that the pair of jaws are moved apart.

The disclosure provides: a laparoscopic forceps comprising: a handpiece including a distal end portion; a tubular member protruding from the distal end portion of the handpiece, the tubular member having a distal end, a pair of jaws having legs that are disposed within the tubular member and partially protruding from the distal end of the tubular member, the pair of jaws and the tubular member being movable relative to each other in a direction parallel to a longitudinal axis of the tubular member; wherein each of the pair of jaws has an arcuate section, and the pair of jaws are closable by advancing the tubular member over the arcuate section of the jaws; and an operable mechanism for creating relative motion between the pair of jaws and the tubular member along a direction parallel to the axis of the tubular member, wherein at least the distal end of the tubular member has a profile shape that is non-circular.

A laparoscopic forceps comprising: (a) a handpiece; (b) a jaw bias mechanism; (c) a tubular member including: (i) an outer tube, and (ii) an inner tube, wherein the outer tube and inner tube are configured for relative axial motion when acted upon by the jaw bias mechanism; and (d) two or more jaws that extend out of the tubular member and the two or more jaws pivot on a common axis that is anchored to the inner tube; wherein the outer tube, during actuation of the jaw bias mechanism, overruns the two or more jaws so that the two or more jaws are moved towards bias.

A laparoscopic forceps comprising: (1) a handpiece; (2) a jaw bias mechanism; (3) a tubular member including: (i) an outer tube, and (ii) an inner tube, wherein the outer tube and inner tube are movable relative to each other when acted upon by the jaw bias mechanism; (4) jaws extending from the tubular member and at least partially through the tubular member; and (5) a biasing element that biases the inner tube and outer tube relative to each other so that the biasing element biases the jaws open; wherein the jaws pivot on one or more axes that are anchored to the inner tube; and wherein the outer tube overruns the jaws so that the jaws are moved towards each other.

The present teachings provide: the laparoscopic forceps include a camming shaft that is located in the distal end of the tubular member; the one or more spacing members are a pair of opposing pins that include a blade recess therebetween, one continuous spacing member that extends across the distal opening of the tubular member, or both; the one or more spacing members include a generally mushroom shape and/or are crimped material of the tubular member, the camming shaft, or both; the one or more spacing members are one or more bars that extend out of the distal opening of the tubular member along the longitudinal axis of the tubular member; the one or more bars each include a bulbous portion at an end that increases a size of each of the one or more bars so that when the bulbous portion contacts the pair of opposing jaws, the legs of the jaws, or both the jaws are moved apart; the laparoscopic forceps include a blade and the blade has a pin recess that extends along the longitudinal axis of the tubular member, and the one or more spacing members extend through the pin recess so that the blade is extendable and retractable; the jaws include a pivot joint that the jaws rotate about to open and close; an inner tube extends within all or a portion of the tubular member; a biasing mechanism for maintaining the jaws in an open state; the common axis is a pin that connects each of the two or more jaws to the tubular member; the laparoscopic forceps include a blade and the blade includes a pin recess that receives a portion of the pin so that the blade is movable along a longitudinal axis of the tubular member; a spacing member is connected to the outer tube so that the spacing member drives the jaws apart; the profile shape is part of the tubular member and the profile shape of the tubular section geometrically constrains the pair of jaws, the legs of the jaws, or both so that the jaws are moved towards each other as the tubular member is moved along the longitudinal axis of the tubular member; the profile shape is two flat sides that are generally parallel to each other; the profile shape is two opposing scalloped contours that resist lateral movement of the jaws, the legs of the jaws, or both; the scallop contours are generally half circular in shape with a maximum height at substantially a center of a length of the scalloped portion, and wherein the opposing scalloped contours extend towards each other; the profile shape is a pair of flattened surfaces on a top surface and a bottom surface and a pair of flattened surfaces on a pair of opposing side surfaces located adjacent the top and bottom surfaces, and a gap extends between the pair of flattened surfaces on the top and bottom surface and the pair of flattened surfaces on the pair of opposing side surfaces located adjacent the top and bottom surfaces; the gap is a blade recess that is sufficiently large so that a blade of the laparoscopic forceps extend longitudinally through the blade recess and out the distal end of the tubular member; substantially all of the tubular member has a generally circular cross-section and the distal end of the tubular member includes a camming shaft that creates the non-circular profile shape; the camming shaft is connected to an internal wall of the tubular member at the distal end of the tubular member; the distal end of the tubular member includes a plurality of arcuate portions that form a plurality of pockets that each extend around a portion of the jaws, the legs of the jaws, or both; a blade recess extends between at least some of the plurality of pockets; the jaws include a pivot joint that the jaws rotate about to open and close; a biasing mechanism for maintaining the jaws in an open state; a pin is connected to the outer tube that extends between the jaws so that upon movement of the outer tube axially towards a proximal end of the laparoscopic forceps, the pin moves the jaws apart; the jaws include a pivot joint and the pivot joint is connected to one or more pins that are connected to the inner tube so that the one or more axes are the one or more pins; a blade is located in the tubular member and the blade is axially movable into and out of the tubular member; or a combination thereof.

The teachings herein provide forceps to include a device that controls the movement between the two opposing jaws. The present teachings provide a device that assists in biasing the jaws and maintains alignment of the blade. The present teachings provide a device that opens the jaws. The present teachings provide a device that spreads the jaws with sufficient force so that the jaws can be used for dissection. The present teachings provide a device that spreads the jaws and does not interfere with a reciprocating blade.

BRIEF DESCRIPTION OF THE DRAWINGS

FIG. 2A1 illustrates a perspective view of an end of a tubular member;
FIG. 2A2 illustrates a cross-sectional view of the tubular member of FIG. 2A1;
FIG. 2B1 illustrates a perspective view of an end of a tubular member;
FIG. 2B2 illustrates a cross-sectional view of the tubular member of FIG. 2B1;
FIG. 2C1 illustrates a perspective view of an end of a tubular member;
FIG. 2C2 illustrates a cross-sectional view of the tubular member of FIG. 2C11

DETAILED DESCRIPTION

Figure 1:
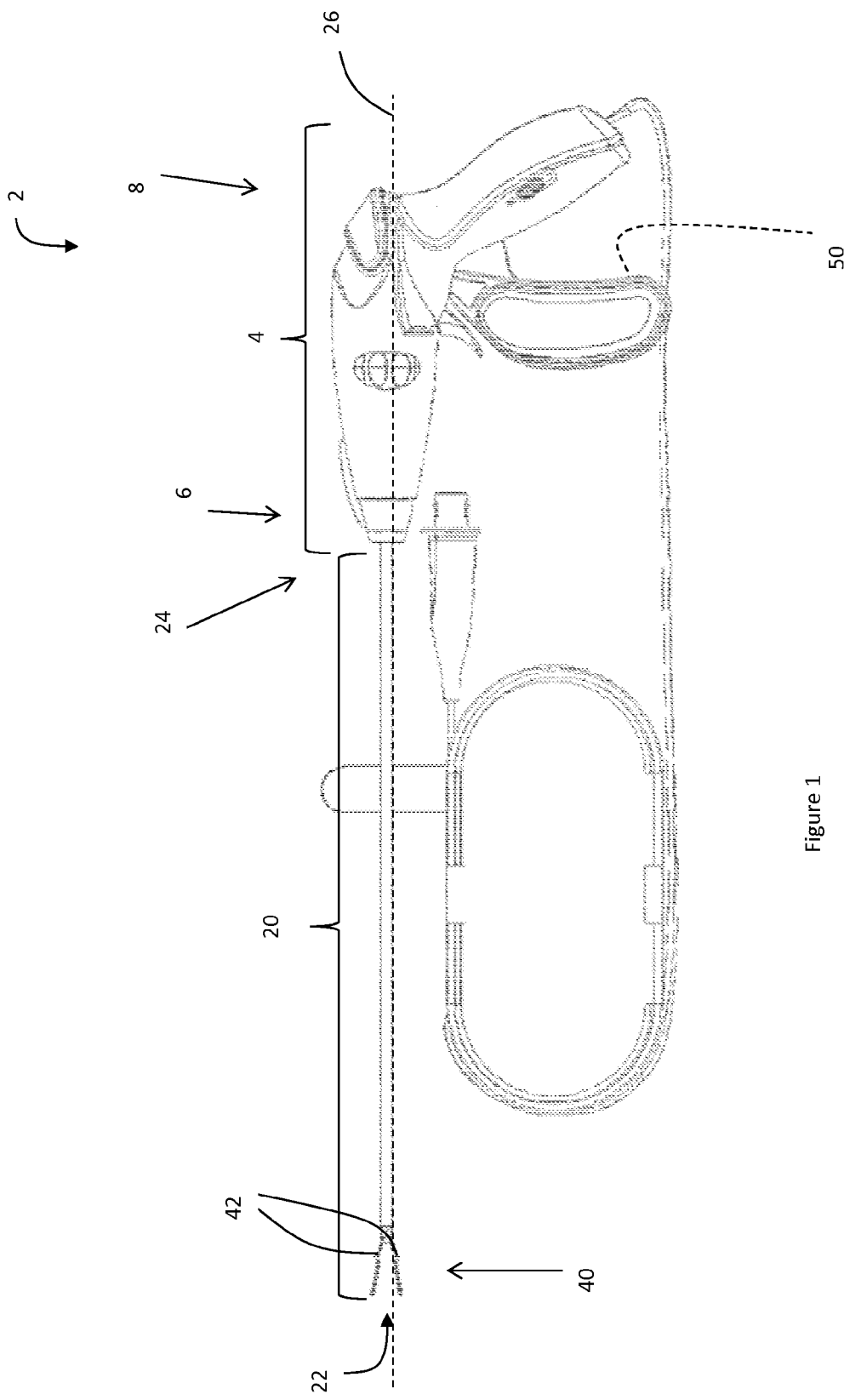
FIG. 1 illustrates a side view of laparoscopic forceps.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings claim priority to U.S. Provisional No. 61/889,060, filed on Oct. 10, 2013 the contents of which are incorporated by reference herein in its entirety for all purposes. The present teachings provide a forceps device. The forceps may function to grip an object. Preferably, the forceps may be used during surgery to grip a feature of interest including: a part of a body, an anatomical feature, tissue, veins, arteries, or a combination thereof. The forceps may function to be used in surgery, for example laparoscopic surgery. The forceps may be used with or without power. Current may be passed through the forceps so that the forceps are used for electrosurgery. For example, a therapy current may be passed from one jaw to a second jaw when tissue is located within the jaw and the therapy current may coagulate blood, cauterize, cut, or a combination thereof. In another example, a therapy current may be passed from one or more of the jaws to a remote electrode (e.g., a return pad). The forceps may generally include one or more working assemblies and sufficient controls to work the one or more assemblies. The forceps may be comprised of parts needed to perform the recited functions and may include generally, a stylet (e.g., a tubular member, a hollow tube, or an assembly of tubes), a hand piece, one or more operable mechanisms used to actuate the stylet, or a combination thereof. The hand piece may be an assembly of parts or housing structures capable of forming a hand piece structure with a cavity.

The hand piece may function to form an enclosing structure for the forceps, a gripping portion for the user, a main portion for manipulating the forceps, or a combination thereof. The hand piece may be any device that houses the working assemblies and parts of the forceps. The hand piece may be comprised of one or more housing structures. Preferably, the hand piece is two or more housing structures. The hand piece may be any structure that is gripped by a user. The hand piece may be any structure that combines one or more of the components discussed herein so that forceps are formed. The hand piece may assist in performing laparoscopic surgery. The hand piece may be ergonomically shaped. The ergonomic shape of the hand piece may be any shape so that the forceps may be used ambidextrously. The ergonomic shape of the hand piece may be any shape such that all the controls can be accessed by a single hand gripping the hand piece. The hand piece may be comprised of housing structures. The housing structures may be one or more devices that form the hand piece. The housing structures may be any devices that may affix certain pieces into position. The housing structures may form a cavity to house working assemblies of the forceps. The housing structures may be one or more housing structures and preferably two or more housing structures. The housing structures may be any device that includes a recess for receiving one or more components of the forceps. The housing structures may house one or more operable mechanisms.

The one or more operable mechanisms may be one or more levers. The one or more operable mechanisms may be any device that may be manipulated or moved by applying pressure to a portion of the one or more operable mechanisms with a hand, finger, foot, or a combination thereof. The one or more operable mechanisms may be any device that may bias other moveable components, for example the tubular member, a cutting assembly, a blade assembly, a functional assembly, or a combination thereof. The one or more operable mechanisms may be biased ambidextrously. The one or more operable mechanisms may be a single operable mechanism that may be linked to two different functions and may be biased to generate each function individually or simultaneously. For example, the operable mechanism may include a double hinged pin and upon movement of the first hinge the jaws may be actuated and upon movement of the second pin the blade may be advanced. Preferably, the one or more operable mechanisms may be two operable mechanisms and each operable mechanism may be biased to perform a different function. The two operable mechanisms may be a clamp operable mechanism and a cut trigger operable mechanism. The combination of two operable mechanisms may include a forked two-sided cam finger, a yoke, or a combination thereof for actuating the one or more jaws, the one or more stylets, or a combination thereof.

The one or more operable mechanisms may include one or more cam fingers. Preferably, each of the one or more operable mechanisms include a single cam finger. The one or more cam fingers may translate movement from a user to the stylet, the blade, the jaws, or a combination thereof. The one or more cam fingers may act upon a portion of the tubular member, the blade assembly, the jaw assembly, or a combination thereof that is located within the hand piece. The one or more cam fingers, the tubular member, the blade assembly, the jaw assembly, or a combination thereof may be moved back to a starting position, moved to a predetermined position, or both once the one or more operable mechanisms are released. The movement back to a starting position, to a predetermined position, or both may be performed by a return mechanism that is in communication with the cam fingers, the operable mechanism, or both.

The return mechanism may assist in actuating one or more assemblies. The return mechanism may return the one or more assemblies to a neutral position and/or a resting position after actuation. The return mechanism may be any device that biases the tubular member and/or stylet to a resting position so that when the tubular member and/or stylet is actuated and released from actuation the tubular member and/or stylet returns back to a resting position. The return mechanism may be and/or include a biasing member (e.g., a spring structure, an elastic member, a compressible member, a stretchable member, any structure that can be compressed and released, or a combination thereof). The return mechanism may be a return spring. The return mechanism may be connected to a proximal end of a stylet, a tubular member, or both. A proximal end of the tubular member may be disposed in the cavity of the hand piece and one or more functional assemblies (e.g., a gripping assembly, a cutting assembly, or both) may be located at a distal end of the stylet, tubular member, or both.

The gripping assembly may function to create a gripping force, grip a feature of interest, or both. The gripping assembly may be one or more devices or parts that provide a gripping force, grips one or more objects, or both. The gripping assembly may be any combination of parts that may be used during surgery to grip one or more features of interest (e.g., tissue, veins, arteries, an anatomical feature, or a combination thereof). The gripping assembly may be actuated by one or more operable mechanisms. The gripping assembly may be used in surgery, for example laparoscopic surgery. The gripping assembly may create a sufficient gripping force so that one or more features of interest of a patient's body may be manipulated by the gripping assembly, secured by the gripping assembly, or a combination thereof. The gripping assembly may be composed of parts that may extend through the tubular member. The gripping assembly may be an assembly of parts rotatable about an axis (e.g., a rotational axis of the gripping assembly, the longitudinal axis of the tubular member, a longitudinal axis of the gripping assembly, or a combination thereof). The gripping assembly may grip and release while being simultaneously rotated. The gripping assembly may be actuated by the actuation mechanism in communication with the gripping assembly. The gripping assembly may be actuated by retracting the two opposing jaws into the stylet (e.g., one or more tubular members) forcing the two opposing jaws closed. The gripping assembly may be actuated by extending the one or more tubular members away from the hand piece so that the one or more tubular members bias the two opposing jaws towards one another into a closed position, creating a gripping force, or both. The gripping assembly may generally have two or more opposing jaws, and one or more jaw shafts or legs, or a combination of both. Preferably, the gripping assembly may have two jaw shafts or legs that each include an arcuate section and an opposing jaw attached to each of the jaw shafts or legs.

The two or more opposing jaws may function to create a gripping force. The two or more opposing jaws may move towards each other to create a gripping force, to grip a feature of interest, or both. The two or more opposing jaws may be any devices that may be used to grip items of interest in surgery, for example laparoscopic surgery. The two or more opposing jaws may function to be used to grip or clamp an item of interest for cutting. The two or more opposing jaws may be any shape and size so that the jaws perform a gripping function, create a gripping force, or both. Preferably, the two or more opposing jaws may be one jaw structure with another mirror image opposing jaw structure (i.e., identical) that when forced together may create a gripping function. The two opposing jaws may be any two or more structures that may be movable relative to each other for perform a gripping function. The two opposing jaws may be any structures that may allow one jaw to be static and one jaw to be movable or any combination thereof. The two opposing jaws may include a gap (e.g., a blade track) to allow for a cutting instrument to be inserted while retaining functionality of the two or more opposing jaws.

The gap may be any shape and size so that a blade, functional element, a surgical instrument, or a combination thereof may be extended into the gap in the jaws, into the gap between the jaws, or both. The blade, a surgical instrument, functional element, or a combination thereof may be extended into the gap formed in (or between) the two opposing jaws while the two opposing jaws are closed, open, or in a position therebetween. The gap may be formed in the opposing jaws, the jaws may be made of a wire material that may be formed to include the gap, material may be removed to form the gap, or a combination thereof. The gap (e.g., blade track) may extend along the longitudinal axis of the tubular member, blade, or both so that the blade axially extends into the gap during use. The material the jaws are made of may be formed to include a gap.

The two opposing jaws may be made of any material so that the two opposing jaws may be used to create a gripping force. The two opposing jaws may be made of a flexible material, resilient material, rigid stainless steel, a plastically deformable material, an elastically deformable material, or a combination thereof. The two opposing jaws may be made of a material that conducts electricity. The jaws may include a protective cover.

The protective cover may function to prevent current leakage, prevent application of power to an undesired location, insulate the wires, create a contact location at a predetermined location, or a combination thereof. The protective cover may protect an outside of the jaws. The protective cover may prevent stray current. The protective cover may assist in directing current to a desired location. The protective cover may be made of an insulating material. The protective cover may be made and/or include rubber, plastic, a polymer, plastic, an insulative material, or a combination thereof. The protective cover may cover only a portion of the jaws so that the jaws may apply power.

The two opposing jaws may be used to apply electricity to a feature of interest that may be gripped by the two opposing jaws. The gripping portion of the two opposing jaws may have a surface texture to grip a feature of interest. For instance the surface texture may be smooth, flat, contoured, serrated, textured, include ridges, mouse teeth, or a combination thereof. Preferably, the gripping portion of the two opposing jaws may have a serrated edge to allow for more secure gripping. The two opposing jaws may have an edge with a surface that may function similar to a serrated edge to allow for secure gripping. The two opposing jaws may be biased from an open position to a closed position by retraction of one of the one or more jaw shafts, movement of the one or more tubular members towards the distal end, or both along an axis of the one or more tubular members. The two opposing jaws may include a jaw bias mechanism, be part of a jaw bias mechanism, or both. The two opposing jaws may have laterally extending arcuate sections at the proximal end (e.g., heel of the jaw) of the jaws that protrude out from the distal end of the tubular member.

The arcuate sections may function to create a ramped surface that moves the jaws towards each other. The arcuate sections may form a raised surface that is sufficiently large such that the arcuate sections do not fit within the stylet, tubular member, or both. The arcuate sections may be formed into the jaw shaft or legs of the jaw shafts. The arcuate sections may be a portion added to the jaw shaft, the legs, or both. The arcuate sections when the jaws are closed may have a largest dimension that is larger than an inner largest opening of the stylet, tubular member, or both. Preferably, at least a portion of the laterally extending arcuate sections are wider than the mouth of the tubular member so that axial movement of the tubular member, the jaw shafts, or both biases the two opposing jaws closing the two opposing jaws, creating a gripping force, or both. For example, when an operable member is actuated the one or more tubular members may be moved towards (i.e., away from the hand piece) the two opposing jaws and may bias the two opposing jaws towards each other. The one or more jaws may be free of one or more arcuate segments. A proximal end of the two opposing jaws of the gripping assembly may each be attached to one or more legs, one or more jaw shafts, or both.

The one or more legs, one or more jaw shafts, or both may function to assist a user in aligning a feature of interest between two or more opposing jaws, assist in creating a gripping force between the two opposing jaws, provide support to one or more jaws, extend through one or more tubular members and/or tubular members, or any combination thereof. The one or more legs, one or more jaw shafts, or both may extend through a central portion of the tubular member and the one or more legs, one or more jaw shafts, or both are movable relative (i.e., parallel, axially, or both) to the tubular members. The one or more legs, one or more jaw shafts, or both may be generally any shape that will perform the recited functions. The one or more legs, one or more jaw shafts, or both may be any light weight material that is strong enough to support the two opposing jaws and to support the gripping action of the jaws. The one or more legs, one or more jaw shafts, or both may be a solid cylindrical rod shape, a hollow cylindrical rod shape, a half circle shape, or a combination thereof. The one or more legs, one or more jaw shafts, or both may include one or more flat portions, may include non-arcuate portions, may be asymmetrical, or a combination thereof. The one or more legs, one or more jaw shafts, or both may be flexible, rigid, conductive, elastically deformable, or a combination thereof. Preferably, the one or more jaw shafts may be a hollow tube. More preferably, the one or more legs, one or more jaw shafts, or both may form the jaw and fold back upon itself to form an opposing leg of the jaw. For example, the leg may extend out of the tubular member and curve back into the tubular member so that the portion extending out of the tubular member forms the jaws. The one or more legs, one or more jaw shafts, or both may extend through and out the tubular member at the distal end of the tubular member at the proximal end of the tubular member, or a combination thereof. The one or more legs, one or more jaw shafts, or both may extend out of the distal end of the tubular member and may have a functional attachment connected to the distal end of the one or more legs, one or more jaw shafts, or both. The functional attachment may be connected to one or both of two opposing jaws or an attachment with the functional equivalent of performing a gripping function. The one or more jaw shafts and/or one or more legs may be adjacent to, extend along opposing sides, surround, or a combination thereof the cutting assembly inside the tubular member. The one or more jaw shafts may terminate in a distal end region of the tubular member, an inner tube, or both.

The one or more jaw shafts may include a pivot joint. The pivot joint may be a joint that connects the jaws to a pin, in inner tube, a tubular member, a camming shaft, or a combination thereof. Preferably, the pivot joint connects the jaw shaft to a pin in the inner tube. The pivot joint may function to connect the jaw shafts so that the jaw shafts are rotatable about an axis that extends through the pivot joint. The pivot joint may extend in a central region of the tubular member (e.g., down a center), along one or more side walls (e.g., along edges), or both. The pivot joint may be a through hole that receives one or more pins, rivets, connection points, bolts, screws, or a combination thereof. The pivot joint may be a pin, rivet, connection point, bolt, screw or a combination thereof that extends from the jaw into contact with the tubular member, the inner tube, the camming shaft, or a combination thereof. The pivot joint may function to create one or more points of contact that the jaws rotate about. The pivot joint may include one or more biasing devices that may move the jaws apart, move the jaws to an open position, move the jaws to a neutral position (which may be an open position), or a combination thereof. The pivot joint may be located so that one or more functional elements, one or more blades, one or more cutting assemblies, or a combination thereof extend out of the tubular member, inner tube, camming shaft, or a combination thereof. The jaws may be biased by one or more jaw bias mechanisms.

The jaw bias mechanisms may function to move the jaws from an open position to a closed position. The jaw bias mechanisms may function to create a closing force, a gripping force, or both. The jaw bias mechanism may function to actuate the jaws closed without the need for any other devices or features. The jaw bias mechanism may function to bias the jaws closed, bias the jaws open, or both. The jaw bias mechanism may only close the jaws. The jaw bias mechanism may be a combination of one or more hollow tubes (e.g., a tubular member or an outer tube), one or more arcuate sections, or preferably a combination of both. The jaw bias mechanism may cause the jaws to rotate about an axis. A jaw bias mechanism may be in communication with each jaw individually. The jaw bias mechanism may be a jaw closure mechanism. The jaw closure mechanism may work in conjunction with a cutting assembly.

The cutting assembly may be any assembly of parts capable of cutting. The cutting assembly may function to cut tissue, veins, arteries, an anatomical feature, a feature of interest, or a combination thereof during a surgical procedure. The cutting assembly may be any cutting assembly that may be used in surgery, for example laparoscopic surgery. The cutting assembly may be an assembly of parts that may fit inside the tubular member and/or tubular member, extend through the stylet and/or tubular member, extend between the pair of opposing jaws, extend between legs, extend between legs and jaws, extend between jaw shafts, extend between jaws, or a combination thereof. The cutting assembly may be any assembly of parts capable of rotating independent of the tubular member or in combination with the tubular member. The cutting assembly may be actuated to perform a cutting function by an actuation mechanism. The cutting assembly may be any cutting assembly that may generally be comprised of a blade, a blade shaft, or a combination thereof.

The blade may function to cut a feature of interest. The blade may be any cutting tool that may be used in surgery, for example laparoscopic surgery. The blade may be any cutting device that may be extended and retracted through the tubular member. The blade may be made of any material that may be sharpened; is strong enough to cut a feature of interest; is biocompatible; that may conduct electricity; or a combination thereof. The blade may be any shape so that the blade may fit inside the tubular member and extend into the gap formed between the two opposing jaws, between two legs connected to a jaw, or both so that a feature of interest may be cut. The blade may be substantially solid along its length. The blade may have a length so that the blade is sufficiently long to cut a feature of interest. The maximum length of the blade may be equal to the length of the jaws. The length of the blade may be substantially equal to that of the protrusions of the camming shaft. The length of the blade may be less than that of the protrusions. The blade may include one or more recesses. The blade may include a pin recess so that a spacing member, a pin, or both may extend through the blade and the blade may still axially move. The pin recess may function to allow the blade to axially move. The pin recess may be a through hole in the blade. The pin recess may have a shape that is substantially identical to that of the spacing member, a pin, or both. The pin recess may be round, oval, a slot, a slit, or a combination thereof. The pin recess may function to allow the blade to fully extend when the jaws are open, the jaws are closed, or a position therebetween. The pin recess may have a length that is substantially equal to the axial movement of the tubular member, the jaws, or both. The blade may be sufficiently small so that the blade may be housed in the tubular member during movement, insertion, or both. The blade may be extended into, and retracted from, the gap in the two opposing jaws. The distal end of the blade may have a shaped edge. The proximal end of the blade may be attached to a blade shaft.

The blade shaft may function to support the blade and assist in moving the blade axially. The blade shaft may extend the blade axially along the axis of the tubular member, the tubular member, or both and out of the tubular member, tubular member, or both (e.g., into the gap formed by the two opposing jaws). The blade shaft may function to extend and/or retract the blade via an operable mechanism. The blade shaft may be used to actuate a blade during surgery. The blade shaft may be of shape and size to actuate a blade inside a tubular member. For example the blade shaft may be a wire, shaped metal, a rod, a plurality of combined longitudinal pieces, or any similar rigid structure that may fit in and extend through the tubular member. The blade shaft may be made of a material that is lightweight, but strong enough to extend a blade through a feature of interest thereby cutting the feature of interest. The blade shaft has a distal end and a proximal end. A blade may be attached to a distal end, a distal end region, or both of the blade shaft. The blade shaft may have a structure at the proximal end of the blade shaft, at the proximal end region of the blade shaft, or both to assist in rotation of the blade inside of the stylet, tubular member, or both.

The stylet as discussed herein may include a tubular member or may be the tubular member. The stylet may include a tubular member and an inner tube. The stylet may include a tubular member that extends around all or a portion of an inner tube. The tubular member may function to extend into a patient during a surgical procedure so that a user (i.e., surgeon) can perform one or more surgical procedures. The tubular member may be flexible so that the tubular member may be moved within a patient. Preferably, the tubular member may be substantially rigid so that the tubular member may be moved to a desired location. The tubular member includes a distal end and a proximal end. The distal end may be an end of the tubular member that is located farthest from the hand piece (e.g., the end of the tubular member that is inserted into a patient). The proximal end of the tubular member may be the end of the tubular member located proximate to the user, in the hand piece, or both. For example, the proximal end may extend into the hand piece so that manipulation of the one or more operable mechanisms manipulates the tubular member. The tubular member and its components may be made of any biocompatible material, for example, stainless steel, plastic, a synthetic material, a natural material, or a combination thereof. The tubular member may comprise a tubular member sub-assembly. The tubular member sub-assembly may include one or more hollow tubes, one or more inner tubes, one or more outer tubes, one or more gripping assemblies, one or more cutting assemblies, one or more rotation mechanisms, one or more operable mechanisms, one or more camming shafts, one or more guides, one or more spacing members, or a combination thereof.

The one or more outer tubes may function to close the jaws, bias the jaws, or both. The one or more tubes may function to bias the actuation mechanisms that bias the jaws. The one or more tubes may function to protect the inner tube. The one or more jaws may move relative to the inner tube. The one or more jaws may axially move towards the distal end and the proximal end during movement. The one or more jaws may overrun the inner tube, the jaws, the arcuate sections, or a combination thereof to bias the jaws towards each other.

The one or more inner tubes may function to create a point of contact for one or more jaws. The one or more inner tubes may function to connect to a camming shaft. The one or more inner tubes may function to extend through all or a portion of the tubular member. The one or more inner tubes may form a connection point, include a connection feature (e.g., a pin, bolt, screw, rivet, or a combination thereof) for one or more jaws. The one or more inner tubes may connect to a pivot joint of one or more jaws so that the one or more jaws rotate about an axis. The one or more inner tubes may assist in opening and closing the jaws. The one or more inner tubes may be located distal of one or more hollow tubes. The one or more inner tubes may be part of a tubular member. The one or more inner tubes may be movable relative to an outer tube. The one or more inner tubes may be axially movable, rotationally movable, or both relative to an outer tube, a camming shaft, or both. The one or more inner tubes may be static and an outer tube may be movable relative to the inner tube. The one or more inner tubes may be substantially the same length as an outer tube. The one or more inner tubes may be shorter than an outer tube. The one or more inner tubes may be in communication with a camming shaft. The one or more inner tubes may receive all or a portion of a hollow tube. The one or more inner tubes may be located between a tubular member and a hollow tube.

The one or more tubular members may include and/or be one or more hollow tubes and the one or more hollow tubes (e.g., an inner tube, an outer tube, or both) may function to house one or more working components (e.g., a gripping assembly, a cutting assembly, or both). The one or more tubular members may function to house all or a portion of one or more functional members (e.g., inner tube, blade, jaws). The one or more tubular members may be any device that may be used to extend a forceps device and any assemblies into a patient. The one or more tubular members may assist in actuating a gripping assembly. The one or more tubular members may be a cannula. The one or more tubular members may be flexible. The one or more tubular members may include a curve, a bend, or a combination thereof. Preferably the one or more tubular members may be rigid. More preferably, the one or more tubular members are generally linear and are substantially rigid. The one or more tubular members may be any hollow tube shaped structure that may rotate around a longitudinal axis, its own longitudinal axis, or both. The one or more tubular members may include a distal end and a proximal end. The one or more tubular members may include an inner circumscribed diameter and an outer circumscribed diameter. The one or more tubular members may include a main body with a consistent inner and outer circumscribed diameter and a tapered portion with a larger outer circumscribed diameter than the main body. The one or more tubular members, the camming shaft, or both may include one or more segments that are square, rounded, oval, irregular, or any shape that allows for the circumscribed diameter of the one or more tubular members to increase and that may allow for rotation around a longitudinal axis, or a combination thereof. The one or more tubular members may include an inner cross-sectional dimension that assists in the functioning of the one or more assemblies.

The inner cross-sectional dimension may be about 1 mm or more, preferably 3 mm or more, more preferably 5 mm or more. The inner circumscribed diameter may be about 20 mm or less, preferably about 15 mm or less, or more preferably about 10 mm or less. The inner circumscribed diameter may from about 1 mm to about 20 mm, preferably from about 3 mm to about 15 mm, or more preferably from about 5 mm to about 10 mm. The inner cross-sectional dimension may vary from location to location within the one or more tubular members and/or camming shaft. The tubular member and/or camming shaft may have a largest cross-sectional dimension and a smallest cross-sectional dimension. The largest inner cross-sectional dimension may be a factor of 2 or more, 3 or more, 4 or more, or even 5 or more times that of the smallest inner cross-sectional dimension. The inner cross-sectional dimension may be substantially the same size as one or more jaw shafts, one or more legs of a jaw, two jaw shafts, two or more legs of a jaw, a blade, or a combination thereof. The inner cross-sectional dimensions may vary to accommodate one or more jaw shafts, leg of a jaw, one or more blades, one or more blade shafts, or a combination thereof. A gripping assembly, a blade assembly, or both may extend through the inner cross-sectional dimension of the one or more tubular members, the camming shaft, the camming shaft, or a combination thereof. The tubular member may be substantially circular, substantially oval, or both along all or a portion of its length. The tubular member may be substantially circular from a proximal end to a region approaching the distal end region. The tubular member may include one or more contour features toward the distal end region.

The one or more contoured features may laterally contain movement of the jaws so that the jaws are forced together, towards a center plane (e.g., a plane that extends substantially down the center of the camming shaft and/or tubular member, a plane that extends between two opposing jaws, or both), or both. The geometry of the one or more contoured features may affect how the jaws are moved. The distal end region may include one or more contour features that vary the size, shape, geometry, orientation, or a combination thereof of the distal end region. For example the one or more contour features may create a flat surface on the outside of the tubular member; may include one or more flat walls on the inside or outside of the tubular member; may include arcuate segments that are non-continuous so that a non-circular, non-linear surface is formed; or a combination thereof. Preferably, the distal end, distal end region, or both of the camming shaft, the tubular member, or both are non-circular, have non-circular portions, or both. The one or more contour features may be one or more flat portions, one or more scalloped portions, one or more blade recesses, one or more pocket surfaces, one or more protrusions, one or more molded flares, one or more side walls, or a combination thereof, and each of the contour features discussed herein may be applied to the tubular members, the hollow tubes, the camming shaft, or a combination thereof. For example, the camming shaft and/or tubular member may be square in shape.

The tubular member, camming shaft, or both may include one or more flat surfaces and/or flattened surfaces located on the inside and/or outside of the tubular member and/or camming shaft. The tubular member, camming shaft, or both may only include one or more flat surfaces on the inside. The flat surfaces may be located anywhere along the length of the tubular member and/or camming shaft. Preferably, the flat surfaces are located in a distal end region. However, the flat surfaces may be located outside of the distal end region. For example, the distal end region may be generally circular and a region on a proximal side of the distal end region may include one or more flat surfaces. The flat surfaces may be located on one or more adjacent walls. Preferably, the flat surfaces are located on opposing sides. The flat surfaces may be located within the tubular member and/or camming shaft so that a jaw having two or more legs and/or shafts has one leg and/or shaft in contact with one flat surface and another leg and/or shaft in contact with a different flat surface. However, both legs and/or shafts may both be in contact with a single flat surface. The tubular member, camming shaft, or both may include one or more, two or more, three or more, four or more, six or more, eight or more, or even ten or more flat surfaces. The flat surfaces may extend around an inside of the tubular member and/or camming shaft so that the tubular member and/or camming shaft has a triangular shape, square shape, rectangular shape, pentagonal shape, hexagonal, heptagonal, octagonal, decagonal, or a combination thereof. The flat surfaces may be spaced apart. For example, two adjacent flat surfaces may be separated by a blade recess. The flat surfaces may be connected together by arcuate surfaces, other flat surfaces, concave portions, convex portions, or a combination thereof. The one or more tubular members and/or camming shafts may be free of, without, exclude, or a combination thereof flat surfaces. Preferably, the tubular members and/or camming shaft include flat surfaces and arcuate surfaces to form one or more scalloped portions.

The one or more scalloped portions may function to control movement of the one or more legs, one or more jaw shafts, or both. The one or more scalloped portions may constrain the one or more legs, the one or more jaw shafts, or a combination of both. The one or more scalloped portions may move two opposing legs, one or more jaw shafts, or both towards each other when the jaws are being actuated, thereby resisting lateral or outward movement of the two opposing legs, one or more jaw shafts, or both with respect to the scalloped portions. The scalloped portions may extend towards a center of the tubular member from an outer edge and/or circumference of the tubular member. The scalloped portions may extend around a portion of the one or more blades. The scalloped portions may become more constraining as the scalloped portion extends towards the distal end. The scalloped portions may be substantially the same dimensions along the length of the scalloped portion. The scalloped portions may be generally concave and extend inward from an outer edge of the tubular member and/or camming shaft. The scalloped portions may reduce the distance from one side of the tubular member and/or camming shaft to the other side relative to an area that does not include the scalloped portion. The scalloped portions may guide the blade through a gap in the jaws, a gap between the jaws, or both. The one or more scalloped portions may form a pockets and/or pocket surface.

The one or more pocket surfaces may function to guide one or more legs, one or more jaw shafts, or both. The one or more pocket surfaces may function to assist in closing the one or more jaws, creating a gripping force, or both. The one or more pocket surfaces may align one jaw relative to another jaw. Each leg and/or jaw shaft may be at least partially surrounded by its own pocket surface (e.g., at least about 90 degrees or more, about 120 degrees or more, or even about 180 degrees or more of each leg and/or jaw shaft is in contact with a pocket surface). The pocket surface may substantially mirror the shape of each leg and/or jaw shaft. The pocket surface may only extend around one side of each leg and/or jaw shaft and the opposing side may be free of a pocket surface so that each leg and/or jaw shaft is free to move towards and/or into contact with an opposing leg and/or jaw shaft. The pocket surfaces may be connected by flat portions (e.g., linear portions). For example, the hollow tube, tubular member, camming shaft, or a combination thereof may include one or more pocket surfaces that have an inner cross-sectional dimension that is substantially the same length as that of the jaw shafts and/or legs of the jaws (i.e., the distance from one side of a pocket surface to the other side of the pocket surface may be substantially the same as the combined largest dimension of the legs of the jaws, jaw shafts, or both). The one or more pocket surfaces may include a blade recess that separates one or more pocket surfaces from another of the one or more pocket surfaces.

The one or more blade recesses may function to guide the blade through the tubular member, the camming shaft or both. The one or more blade recesses may prevent the blade from contacting the jaws, the legs, the jaw shafts, or a combination thereof. The one or more blade recesses may substantially mirror the shape of the blade. The one or more blade recesses may include one or more flat portions, one or more arcuate portions, or both. The one or more blade recesses may extend along a center plane. The one or more blade recesses may include a space so that a portion of each of the legs, each of the jaw shafts, or both extend at least partially into the blade recess. The one or more blade recesses may be a gap in a flat portion, a flat wall, or both. The one or more blade recesses may be at any location along the tubular member, the camming shaft, or both. Preferably, the blade recess is located within the distal end region of the tubular member, the camming shaft, or both. The one or more blade recesses, one or more contour features, or both may be used in conjunction with and/or be placed relative to one or more guides.

The one or more guides may be any device that supports one or more legs, one or more shafts, one or more wires, one or more functional elements, or a combination thereof as they extend from a proximal end to a distal end. The one or more guides may support a control portion of one or more functional elements (i.e., a portion that is actuated or actuates to create a predetermined result). For example, a leg of a jaw may extend through the guide and the guide may provide support and/or isolation so that the leg of one jaw is not intertwined and/or damaged by a leg of another jaw. The one or more guides may prevent bending, kinking, coiling, intertwining, damage, or a combination thereof as elements extend through the tubular member. The one or more guides may include one or more through holes for guiding one or more members. The one or more through holes may be a one or more blade shaft guides, one or more jaw shaft guides, one or more functional element shaft guides, or a combination thereof. The one or more guides may be used in conjunction with the one or more contour features in the distal end region of the tubular member, the camming shaft, or both. The one or more guides may allow for substantially all of an axial force to be translated axially through the tubular member. The one or more guides may restrict the cross-sectional area of the tubular member along the longitudinal axis of the tubular member. The one or more guides may extend along the length of the tubular member. The one or more guides may extend along the length of the tubular member and stop before reaching the distal end region. The one or more guides may have a length that is about 85 percent or less, about 75 percent or less, about 60 percent or less than the tubular member. The tubular member may work with one or more features of the tubular member, the camming shaft, or both. The tubular member may include, be connected to, be used in conjunction with, be located adjacent to, or a combination thereof one or more camming shafts.

The one or more camming shafts may function to change the shape, configuration, geometry, orientation, or a combination thereof of the one or more tubular members. The one or more camming shafts may be a device that is put in, connected to, fit with, or a combination thereof a distal end region. The one or more camming shafts may constrain the cross-sectional area of the tubular member. The one or more camming shafts may restrict the jaws, the legs of the jaws, the jaw shafts, the arcuate sections, or a combination thereof. The one or more camming shafts may assist in forming a gripping force, a desiccation force, or a combination thereof. The one or more camming shafts may include any of the contour features discussed herein for the tubular member and vice versa. The one or more camming shafts may be connected to the tubular member by friction fit, adhesive, welding (e.g., laser or spot), crimping, a detent, a fastener, an interference fit, threads, or a combination thereof. The one or more camming shafts may include one or more connection features (i.e., a portion that is raised above the remainder of the camming shaft). The one or more camming shafts may include a complex geometry and may vary the geometry of a standard tubular member. For example, a standard tubular member may be created for all applications and a scalloped portion may be added to one tubular member and a pocket surface may be added to a different tubular member by selecting and installing a camming shaft with those features. The one or more camming shafts may be installed within the distal end region of the tubular member so that the distal end region has a changed geometry. However, the one or more camming shafts may extend to a proximal side of the distal end region. The one or more camming shafts may be made of any biocompatible material. The one or more camming shafts may be made of plastic, a polymer, metal, steel, surgical steel, stainless steel, or a combination thereof. The one or more camming shafts may be made of a material that may be formed by molding (e.g., insert molding, blow molding, injection molding, or a combination thereof). The camming shaft may be molded directly to the tubular member. The camming shaft may be connected to the tubular member so that substantially all of the camming shaft is located within the tubular member. The camming shaft may form the distal end region of the tubular member. The camming shaft may have a portion that is connected to and extends from the tubular member. The camming shaft may include one or more protrusions that extend proximal into the tubular member.

The one or more protrusions may function to connect the camming shaft to a distal end of a tubular member so that the camming shaft forms the distal end region of the tubular member. The one or more protrusions may function to guide one or more elements (e.g., a jaw shaft, a leg, a blade shaft, a functional element shaft, or a combination thereof) through the tubular member, into the camming shaft, or both. The one or more protrusions may function to provide axial stiffness to the tubular member. The one or more protrusions may assist in connecting the one or more camming shafts to the tubular member. The one or more camming shafts may be free of protrusions, exclude protrusions, be without protrusions, or a combination thereof. The one or more protrusions may be connected to an end region of the camming shaft, a molded flare, or both.

The one or more molded flares may function to extend into a tip of a tubular member, connect the camming shaft to the tubular member, reduce the cross-sectional area of a distal end region of the tubular member, or a combination thereof.

The one or more molded flares may form a step in the camming shaft. The one or more molded flares may adapt the camming shaft to fit within one or more tubular members. The one or more molded flares may form a series of steps that allow the camming shaft to be inserted into and/or connected to tubular members having a different diameter and/or cross-sectional area. The one or more molded flares may connect the camming shaft to the tubular member so that the outside cross-sectional length of the tubular member and the camming shaft are substantially equal, so that a lip is not formed between the camming shaft and the tubular member, or both. The outer walls of the camming shaft may be generally circular, a geometric shape, symmetrical, asymmetrical, or a combination thereof. The one or more camming shafts may be free of one or more molded flares, exclude a molded flare, or both. The outer walls of the camming shaft may have any of the features discussed herein for the shape of the tubular member. The outer walls and the inner walls of the camming shaft may have a different configuration.

The camming shaft may include one or more of the contour features as are discussed herein. The one or more contour features may be one or more side walls. The one or more side walls of the camming shaft may perform any of the functions and/or include any of the structure discussed herein for the flat portion of the tubular member. The one or more side walls may be contoured, angled, flat, parallel, adjacent, in contact with one or more legs and/or jaw shafts, or a combination thereof. The one or more side walls may include one or more coatings. The one or more coatings may provide electrical insulation between the stylet, tubular member, or both and the legs, jaw shaft, or both. The one or more side walls may be formed of a different material than the camming shaft. The one or more side walls may be connected to, molded on, attached to, adhered to, fastened to, or a combination thereof to the camming shaft. The one or more side walls may be padded. Preferably, the lateral side walls only are padded. The one or more side walls may be made of and/or include a polymer, plastic, elastomer, or a combination thereof. The padding on the one or more side walls may be low friction, high friction, hard, soft, a dampening material, or a combination thereof. The one or more side walls may extend along an inside of the camming shaft, onto an ear of the camming shaft, on a flare, on the protrusions, or a combination thereof.

The one or more ears may function to extend the camming shaft in a distal direction. The one or more ears may function to create a blunt surface, a surface with a smaller area, or both. The one or more ears may provide axial stiffness, radial stiffness, longitudinal stiffness, or a combination thereof to the camming shaft, the tubular member, or both. The shape of the ears may be varied depending on structural strength requirements of the camming shaft. The shape of the ears may include more structure and/or material than other shapes of the ears. The one or more ears may be shaped so that any contact between the ears and tissue does not damage tissue. The one or more ears may be an integral part of the camming shaft. The ears may lengthen the distal end region. The ears may extend out of and/or from a distal end of the camming shaft, the tubular member, or both. The ears may be located on the lateral sides of the camming shaft. The ears may be located so that the jaws open and close without interference from the ears. The one or more ears may be square, circular, oval, include a blunt distal end, include an arcuate distal end, or a combination thereof. The one or more ears may be made of a material that provides axial stiffness to the tubular member, the camming shaft, or both. The one or more ears may include a material on the inside of the camming shaft so that the ears support one or more spacing members. The one or more camming shafts may be free of ears, exclude ears, or both. The one or more ears may include one or more spacing members, be located proximate to one or more spacing members, or a combination thereof.

The one or more spacing members function to separate the jaws. The one or more spacing members may function to separate the jaws when the jaws and/or tubular member is retracted to a starting position, when the jaws and/or tubular member is over retracted (i.e., a position past the starting position). For example, a starting position is considered a zero position and over retracted is considered a negative position (e.g., −1 or more, −2 or more, −5 or more). The one or more spacing members may be located at a distal end of the stylet, tubular member, inner tube, or a combination thereof. The one or more spacing members may be located distal to a connection feature for a pivot joint (e.g., a pin). The one or more spacing members may work in conjunction with a connection feature for connecting a pivot joint to the stylet, inner tube, tubular member, or a combination thereof. The one or more connection features may form a connection with the stylet and the one or more spacing members may rotate the jaws outward (e.g., open) about the connection features. The one or more spacing members may separate the jaws at a neutral position, a starting position, or both. The one or more spacing members may separate the jaws so that the jaws may be used for dissection, separating tissue, or both. The one or more spacing members may assist in moving tissue, spreading tissue apart, or both. The jaws when pressed against the spacing members may create a force of about 1 N or more, about 2 N or more, about 3 N or more, or even about 5 N or more. Stated another way, the jaws may resist closing when a force of about 1 N or more, 2 N or more, 3 N or more, or even about 5 N or more. When the one or more spacing members are in contact with the two or more jaws the spacing members prevent the jaws from closing by external forces. The one or more spacing members may be a single spacing member that extends across the opening of the tubular member, the camming shaft, or both. The one or more spacing members may be a biasing member that creates a positive force against one or both of the jaws so that the jaws are forced apart. The one or more biasing members may function to create a force so that a default position of the jaws is open. The one or more biasing members may be located in contact with the jaws, the jaw shafts, the arcuate sections, a heel, or a combination thereof. The one or more biasing members may be a spring, an elastic material, an expandable material, an elastically deformable material, a bent piece of metal, a helically wrapped material, or a combination thereof. The one or more spacing members may be two spacing members and the two spacing members may extend from opposing sides towards a center, a central plane, or both of the tubular member, camming shaft, or both. The one or more spacing members may alter the pressure exerted by the jaws. The one or more spacing members may alter the pressure exerted from a front of the spacing member to a heel of the spacing member or vice versa depending upon the location of the spacing members, the shape of the spacing members, or both. The one or more spacing members may provide for an even distribution of force along the surface of the jaws relative to jaws that do not include the spacing members. The one or more spacing members may be shaped so that the spacing members are free of contact, free of interference, or both with the jaws when the jaws are closed, a gripping force is created, or both. The one or more spacing members may be connected to the tubular member, the camming shaft, or both. The one or more spacing members may be connected by an adhesive, threads, welding (e.g., spot or laser), a fastener, or a combination thereof. The one or more spacing members are at a location so that when the jaws are closed the spacing member aligns with the arcuate sections. The one or more spacing members may have a uniform shape, a tapered shape, one shape on a distal side and a different shape on a proximal side, or a combination thereof. Any of the spacing members discussed herein may include one or more tapered portions. The tapered portions may allow for axial movement of the jaws without interference with the jaws, shafts, jaw shafts, legs, or a combination thereof.

The tapered portions may extend at a low angle to a point. The tapered portions may be one or more tapered portions. The one or more tapered portions may be one or more fillets. The one or more fillets may be a plurality of fillets that are interconnected to form the tapered portion. The tapered portions may extend at a steep angle and have a blunt end. The tapered portions may be located on the distal side, the proximal side, or both of the spacing members. The tapered portions may extend at an angle of about 5 degrees or more, about 10 degrees or more, about 15 degrees or more, or even about 25 degrees or more. The tapered portion may extend at an angle of about 90 degrees or less, about 75 degrees or less, or about 60 degrees or less. The shape of the spacing member may change across the cross-sectional length of the spacing members. The spacing member may continuously extend across the cross-sectional length of the tubular member, the camming shaft, or both. The spacing member may be two or more discrete pieces and may be connected in two or more locations to the tubular member, the camming shaft, or both. The spacing members may have any shape that assists in separating the jaws, using the jaws for dissection, or both. The spacing members may be a pin, a crimp, a bar, include a bulbous portion, a mushroom pin, a tapered portion, or a combination thereof.

The one or more pins may substantially span the cross-sectional length of the camming shaft, the tubular member, an inner tube, or a combination thereof. The one or more pins, as discussed herein, may be used both as a connection feature and a spacing member. The one or more pins may be two pins that are separated by a gap. The one or more pins may extend through a pin recess in the blade. The one or more pins may be round, extend from an ear, form a distal most point of the tubular member, or a combination thereof. The one or more pins may form a common axis. The one or more pins may form a common axis for the two or more jaws. The two or more jaws may rotate about the pin. The one or more pins may be uniform in shape. When more than one pin is used the pins may be identical. The one or more pins may be a mushroom pin. The one or more pins may include a mushroom portion. The mushroom portion may function to prevent the legs, jaws, jaw shaft, or a combination thereof from extending towards a center, a central portion, or both of the tubular member. The mushroom shape may prevent the legs, jaw shafts, or both from contacting each other, the blade, or both. The mushroom shape may provide a space for the blade to extend through the tubular member without pressure being exerted by the legs, jaw shafts, or both. The mushroom portion may be a part of the pin that is expanded relative to the rest of the pin. The mushroom portion may be a portion that 1.2 times or more, 1.3 times or more, or even 1.5 times or more the size of the non-mushroom portion of the pin. The mushroom portion of the mushroom pin may be located substantially in the center of the camming shaft, the tubular member, or both. The mushroom pin may be substantially the same as a head on a screw, nut, bolt, the like, or a combination thereof. The mushroom pin may be integrally molded. The mushroom pin may be a discrete piece added to the camming shaft, the tubular member, or both. The one or more tubular members, the one or more camming shafts, or both may be free of a pin. The one or more tubular members, the one or more camming shafts, or both may include an integrally formed portion such as a crimp.

The one or more crimps may function to perform the functions of a spacing member. The one or more crimps may be a unitary part of the tubular member, the camming shaft, or both. The one or more crimps may be formed. The one or more crimps may be material folded upon itself. The one or more crimps may be a part that extends in a distal direction from the camming shaft and is formed to extend inward (i.e., in a lateral direction) and is folded together. The one or more crimps may be folded so that the crimps are solid, include a recess, is hollow, or a combination hereof. Preferably, the one or more crimps are cut and folded to extend from and across the tubular member and form a frontal bar. The one or more crimps may be varied in size depending on the cross-sectional thickness of the tubular member, camming shaft, or both. For example, a standard camming shaft with crimping material may be created and the shape and size of the crimp may be varied depending upon the tubular member, the legs, the jaw shaft, or both being used. The crimp may be one solid piece that extends across opening of the tubular member, the camming shaft, or both. The one or more crimps may extend from an outside edge of the tubular member, the camming shaft, or both. The one or more crimps may extend from within the tubular member, the camming shaft, or both. The crimp may be two discrete pieces that extend from opposing sides. The spacing member may be a longitudinally extending bar.

The one or more bars may perform the function of any of the spacing members discussed herein. The one or more bars may extend from an inside of the tubular member, the camming shaft, or both. The one or more bars may extend substantially the length of the camming shaft. The one or more bars may extend from a central portion of the camming shaft axially out an opening in camming shaft. The one or more bars may be substantially planar along their length. A portion of the one or more bars may be substantially planar and a portion of the one or more bars may be bulbous. A portion of the one or more bars located within the camming shaft, the tubular member, or both may be planar and a portion located outside of the camming shaft may form a bulbous portion. The bar may gradually increase in size as the bar extends in the distal direction. The bar may terminate at a bulbous portion. The bulbous portion may be substantially the largest portion of the one or more bars. The bulbous portion may gradually become thicker than a main portion of the bar. The bulbous portion may be a step change from the main portion of the bar. The bulbous portion may have an upper portion and lower portion and the upper portion and the lower portion may be mirror images of each other. The bulbous portion may substantially mirror the shape of the arcuate sections of the jaws. The upper portion and the lower portion may be equal in size so that a jaw extending over the top of the upper portion and a jaw extending under the bottom of the lower portion moves the jaws an equal distance outward. The one or more bars may be integrally connected to the camming shaft, the tubular member, or both. The one or more bars may be integrally formed with formation of the camming shaft, the tubular member, or both. A cross-section of the bulbous portion of the bar may have a tear drop shape. A cross-section of the bulbous portion of the bar may have one portion that is a factor of 2 or more, 3 or more, or even 4 or more larger than the rest of the bar.

FIG. 1 illustrates a side view of an example of laparoscopic forceps 2. The laparoscopic forceps 2 include a handpiece 4 having a distal end 6 and a proximal end 8. The handpiece 4 also includes at least one operable mechanism 50. A tubular member 20 has a proximal end 24 that is connected to the distal end 6 of the handpiece 4. The tubular member 20 includes a distal end 22 that includes jaws 40 extending therefrom. The jaws 40 have arcuate segments 42 that open and close the jaws 40 when the tubular member 20 is moved forward along the longitudinal axis 26 of the tubular member into contact with the arcuate segments 42 or the jaws 40 are moved backwards along the longitudinal axis 26 into contact with the tubular member 20.

FIG. 2A1 illustrates a perspective view of a tubular member 20. The tubular member 20 includes a distal opening 28 for legs of the jaws and the jaws 40 (not shown) to extend from the tubular member 20.

FIG. 2A2 illustrates a cross-sectional view of the tubular member 20 of FIG. 2A1 along lines 2A2-2A2. The tubular member 20 is generally square in shape and includes top and bottom flat portions 30 and opposing flat side wall portions 30. The legs of the jaws 44 extend through the tubular member 20 and the square shape of the tubular member 20 constrains the legs of the jaws 44 so that axial movement of the legs 44 within the tubular member 20 closes the jaws (not shown) reliably one on top of the other.

FIG. 2B1 illustrates a perspective view of a tubular member 20. The tubular member 20 includes a distal opening 28 for legs of the jaws and the jaws 40 (not shown) to extend from the tubular member 20.

FIG. 2B2 illustrates a cross-sectional view of the tubular member 20 of FIG. 2B1 along line 2B2-2B2. The tubular member 20 is generally oblong in shape and includes top and bottom flat portions 30 in a distal region. The legs of the jaws 44 extend through the tubular member 20 and the flat portions 30 of the tubular member 20 constrains the legs of the jaws 44 so that axial movement of the legs 44 or the tubular member 20 closes the jaws (not shown) reliably one on top of the other.

FIG. 2C1 illustrates a perspective view of a tubular member 20. The tubular member 20 includes a distal opening 28 for legs of the jaws and the jaws 40 (not shown) to extend from the tubular member 20.

FIG. 2C2 illustrates a cross-sectional view of the tubular member 20 of FIG. 2C1 along line 2C2-2C2. The tubular member 20 is generally oblong in shape and includes top and bottom scalloped portions 32. The legs of the jaws 44 extend through the tubular member 20 and the scalloped portions 32 of the tubular member 20 constrains the legs of the jaws 44 so that axial movement of the legs 44 or the tubular member 20 closes the jaws (not shown) reliably one of top of the other.

Figure 3:
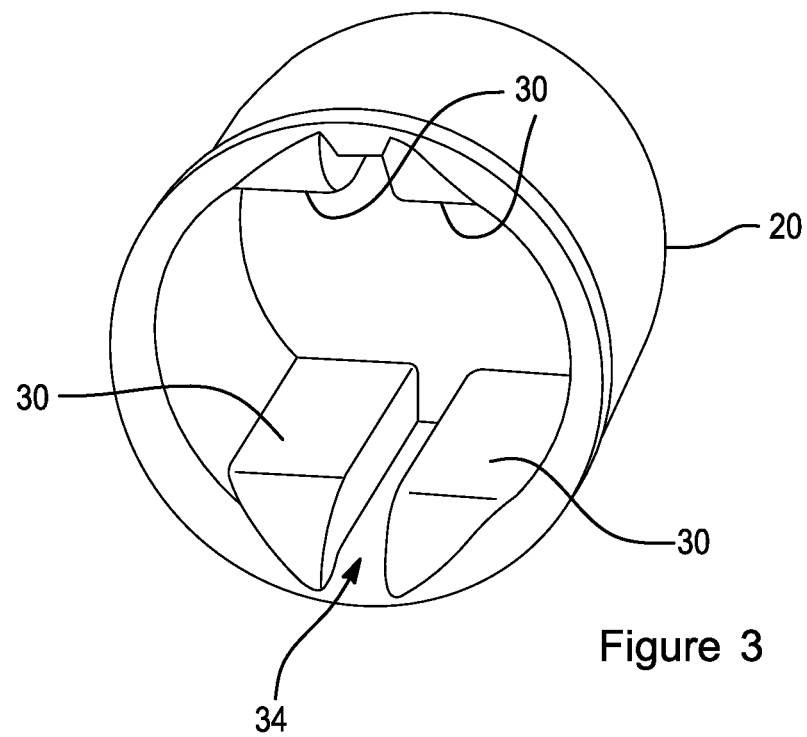
FIG. 3 illustrates an end of a tubular member and/or a camming shaft.

FIG. 3 illustrates an example of an end of the tubular member 20 or a camming shaft that may be placed within the tubular member 20. The tubular member 20 includes a pair of internal flat portions 30 along the top surfaces and the bottom surfaces. A blade recess 34 extends between the pair of internal flat portions 30 so that a blade (not shown) extends out of the tubular member 20.

Figure 4:
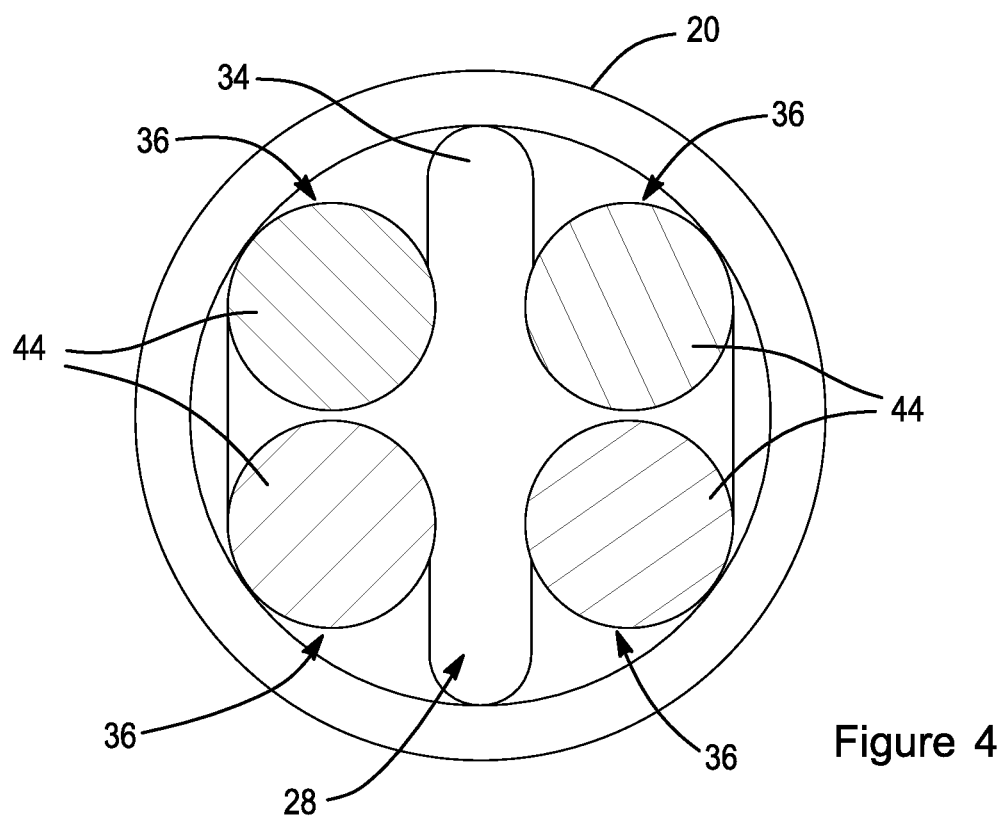
FIG. 4 illustrates an end view of a tubular member and/or a camming shaft.

FIG. 4 illustrates a cross-sectional view of a tubular member 20. The tubular member 20 includes a plurality of pocket surfaces 36. The plurality of pocket surfaces 36 include at least a portion that has a complementary shape to that of the legs of the jaws 44 so that as the tubular member 20 or the legs 44 axially move the pocket surfaces 36 control the orientation and movement of the jaws (not shown). A blade recess 34 extends between the pocket surfaces 36 so that the blade (not shown) extends through the distal opening 28 of the tubular member.

Figure 5:
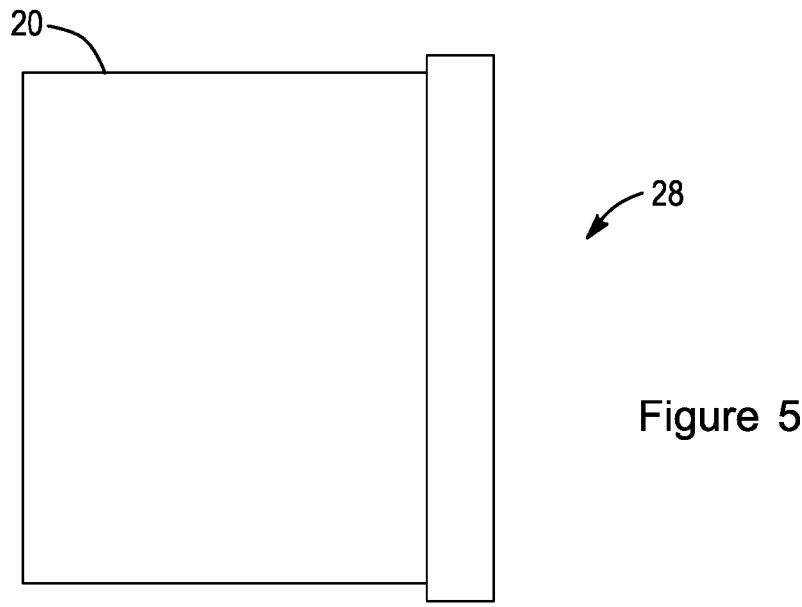
FIG. 5 illustrates a side view of an end of a tubular member and/or a camming shaft.

FIG. 5 illustrates a side view of the tubular member 20 of FIG. 4. As shown, the tubular member 20 has a distal opening 28 at one end.

Figure 6:
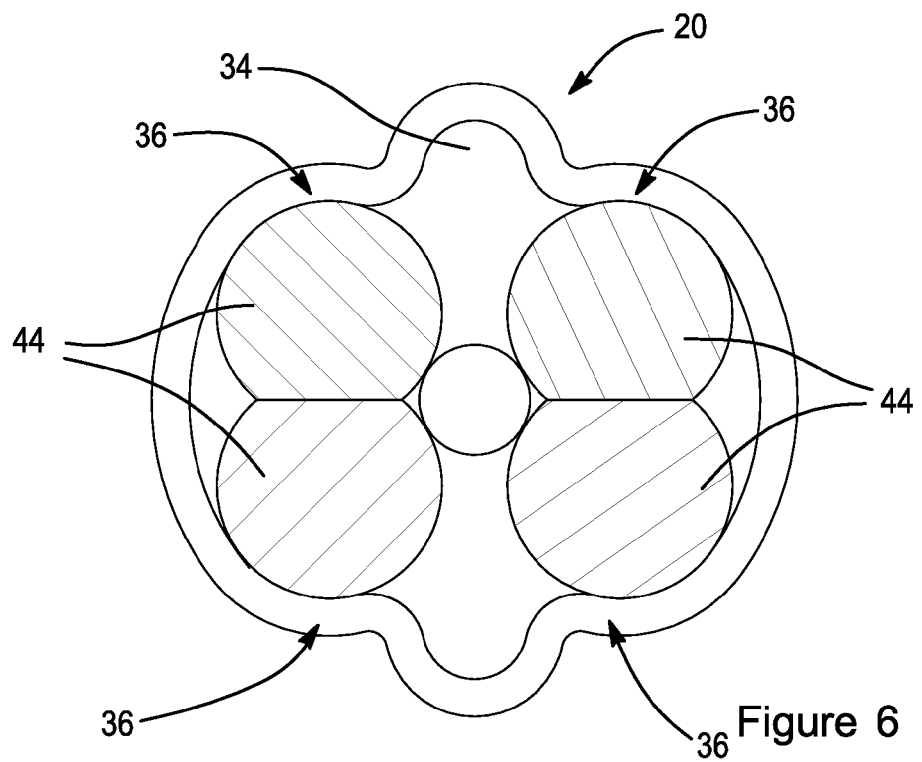
FIG. 6 illustrates a cross-sectional view of an end of a tubular member and/or a camming shaft.

FIG. 6 illustrates another example of a cross-sectional view of a tubular member 20. The tubular member 20 includes a blade recess 34 down the center between the legs of the jaws 44. The tubular member 20 includes a pocket surface 36 for receiving each of the legs of the jaws 44. FIG. 6 as illustrated is taken at a different cross-sectional location as FIG. 4, however. FIG. 4 may be taken at the same cross-sectional location as FIG. 6.

Figure 7:
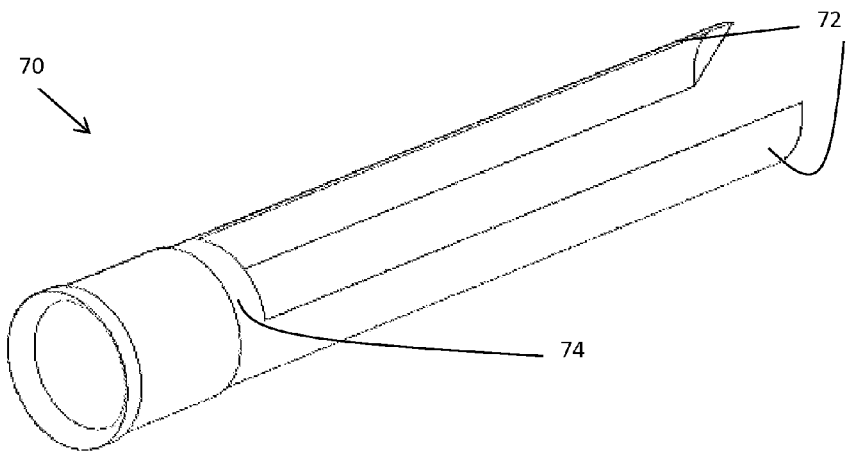
FIG. 7 illustrates a perspective view of a camming shaft.

FIG. 7 illustrates a perspective view of one example of a camming shaft 70 that is inserted into a tubular member (not shown). The camming shaft 70 includes a molded flare 74 with a pair of protrusions 72 extending therefrom.

Figure 8:
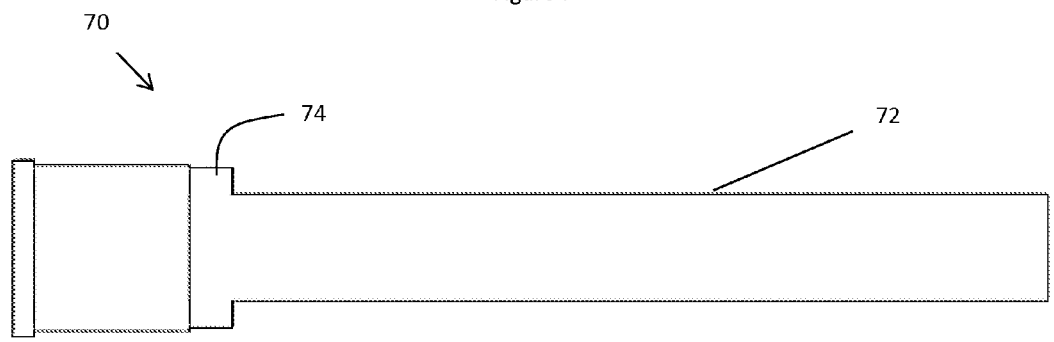
FIG. 8 illustrates a side view of the camming shaft of FIG. 7.

FIG. 8 illustrates a side view of the camming shaft 70 with a molded flare 74 and a pair of protrusions 72 extending from the molded flare 74.

Figure 9:
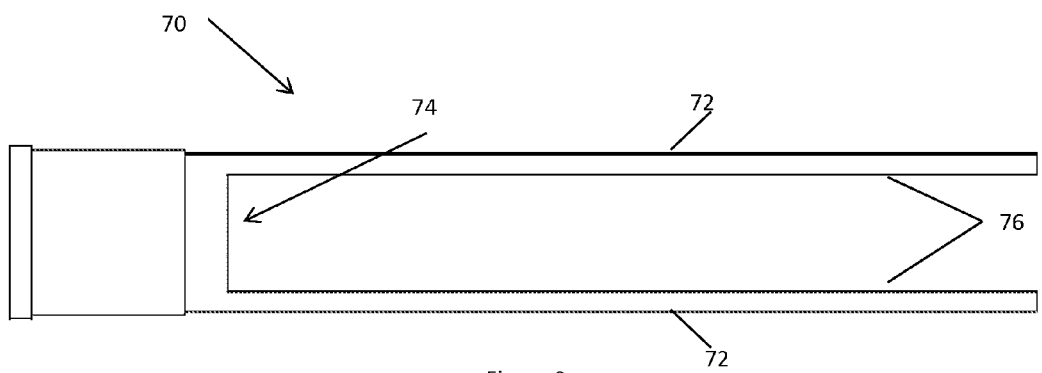
FIG. 9 illustrates a top view of the camming shaft of FIG. 7.

FIG. 9 illustrates a top view of the camming shaft 70. The camming shaft includes a molded flare 74 with a pair of protrusions 72. Each of the protrusions 72 include a sidewall 76.

Figure 10:
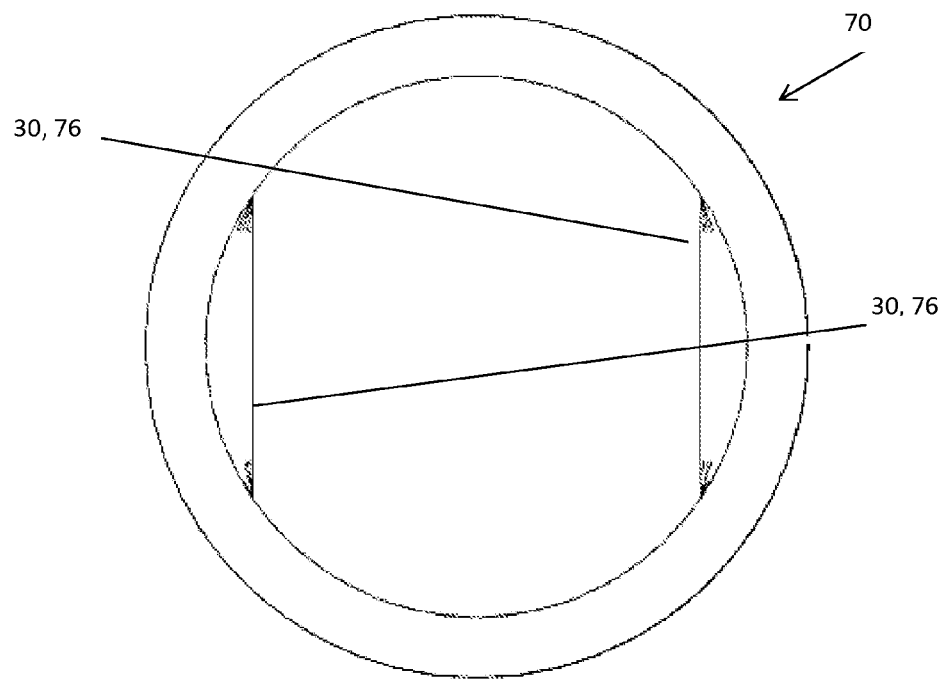
FIG. 10 illustrates an end view of the camming shaft of FIG. 7.

FIG. 10 illustrates an end view of a camming shaft 70. The sidewalls 76 of the camming shaft 70 have a flat portion 30 on the inside of the camming shaft 70.

Figure 11:
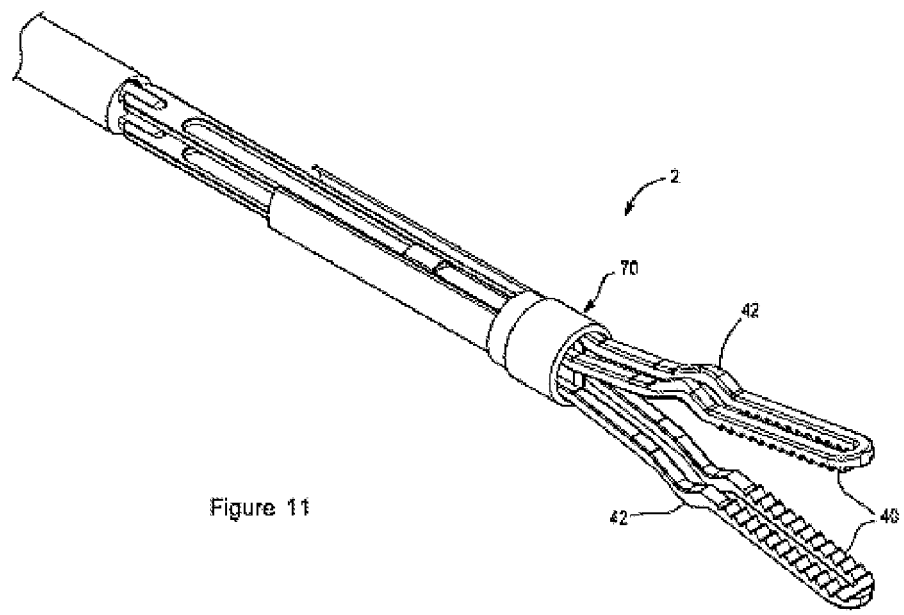
FIG. 11 illustrates an example of jaws extending out of the camming shaft of FIG. 7.

FIG. 11 illustrates a camming shaft 70 located on the laparoscopic forceps 2 with the jaws 40 extending therefrom. The jaws 40 include a pair of arcuate sections 42 that are biased by the camming shaft 70 so that the jaws 40 are opened and closed.

Figure 12:
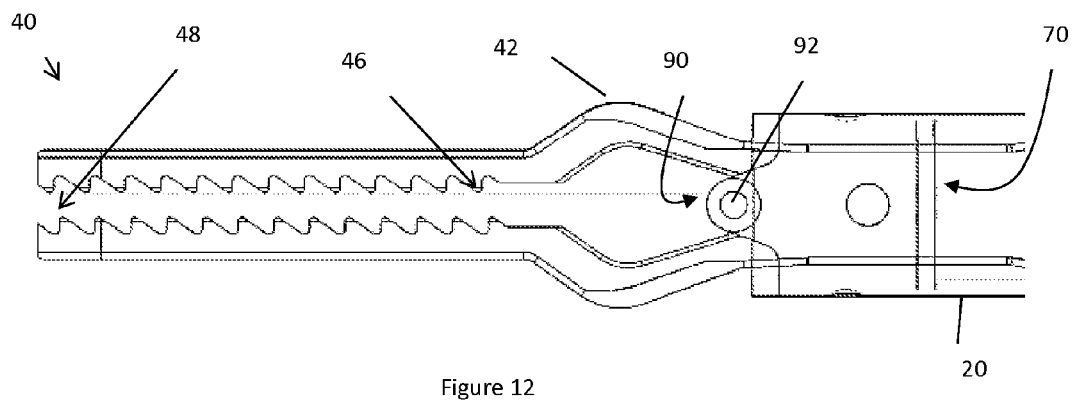
FIG. 12 illustrates a side view of a distal end of laparoscopic forceps shown in transparent.

FIG. 12 illustrates a side view of jaws 40 including a spacing member located between the jaws. The jaws 40 include a heel 46 and a front 48. Proximate to the heel 46 are a pair of opposing arcuate segments 42 that close the opposing jaws 40 when the shaft 20 is moved into contact with the opposing jaws 40. When the shaft 20 is retracted a spacing member 90 located on a camming shaft 70 moves the jaws 40 apart. The spacing member 90 is a pair of pins 92 that extend from the camming member 70.

Figure 13:
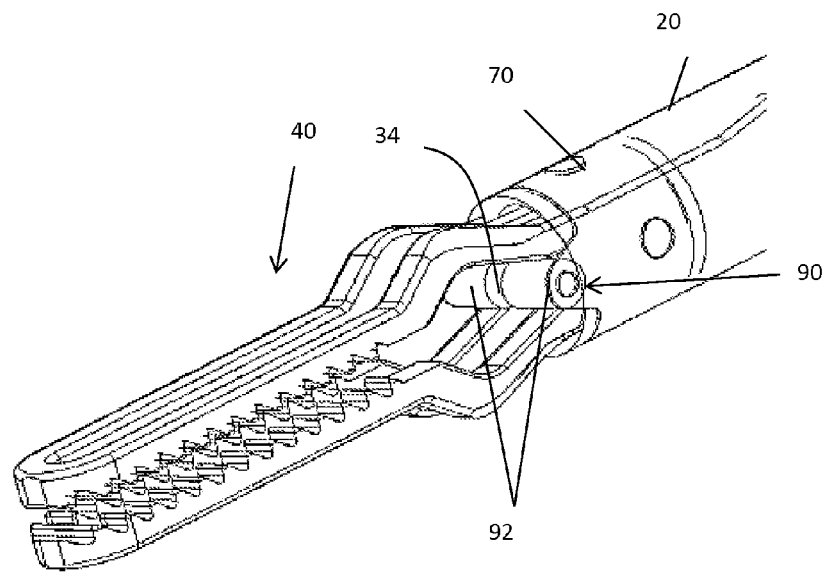
FIG. 13 illustrates a perspective view of laparoscopic forceps shown in transparent.

FIG. 13 illustrates a perspective view of the jaws 40. The jaws 40 are closed by the tubular member 20 being moved into a forward position. The tubular member 20 includes a camming shaft 70 with a spacing member 90. The spacing member 90 is a pair of pins 92 that are cantilever and extend from the camming shaft 70 so that a blade recess 34 is located between the two cantilever pins 92.

Figure 14A:
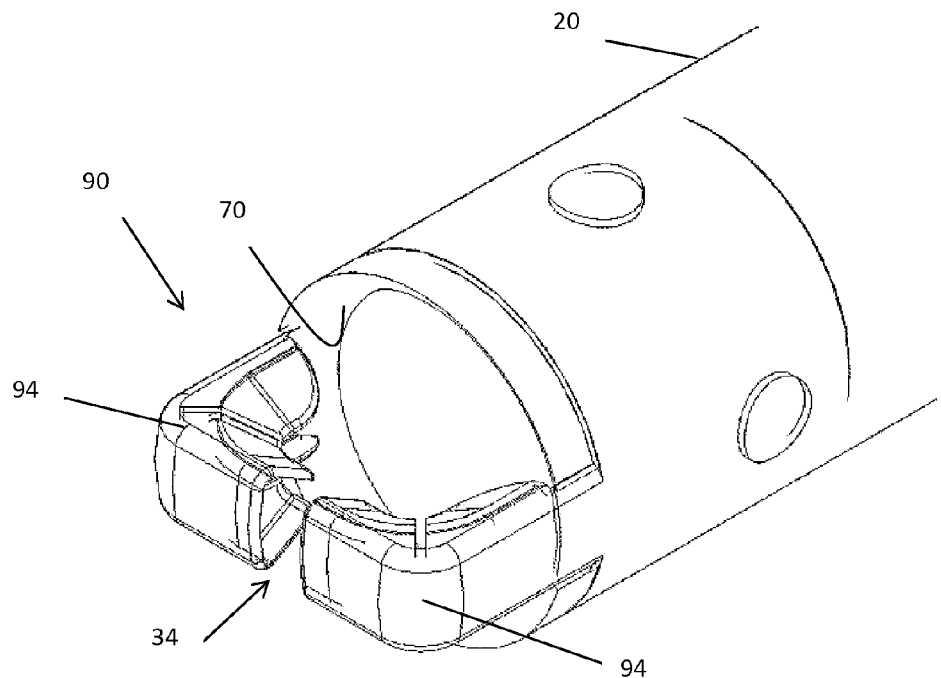
FIG. 14A illustrates a perspective view of a spacing member.

FIG. 14A illustrates a perspective view of another example of a spacing member 90. The spacing member 90 extends from a camming shaft 70 that is connected to a tubular member 20. The spacing members 90 are crimps 94 that are formed by folding material together. The crimps 94 include a blade recess 34 therebetween so that a blade (not shown) can extend between the crimps 94.

Figure 14B:
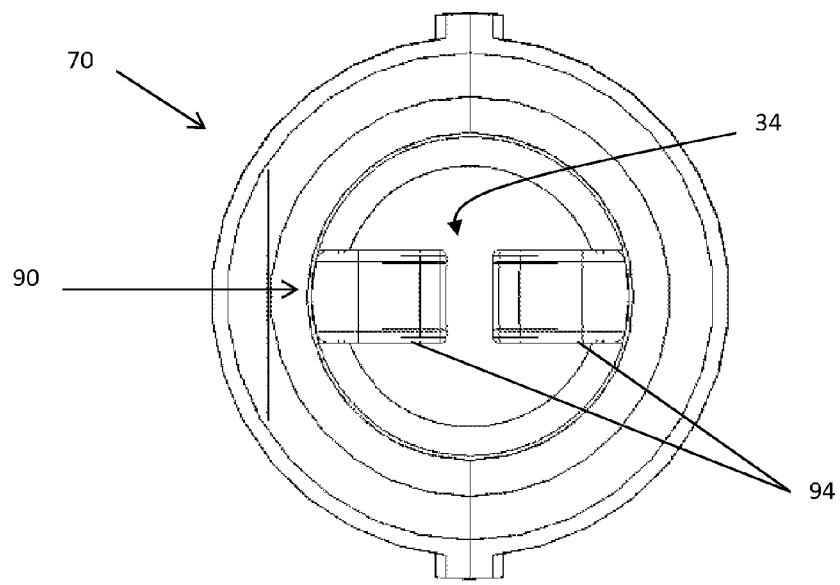
FIG. 14B illustrates an end view of the spacing member of FIG. 14A.

FIG. 14B illustrates a plan view of an opening in the camming shaft 70. The camming shaft 70 includes a pair of spacing members 90. The pair of spacing members 90 are crimps 94 with a blade recess 34 extending therebetween.

Figure 15:
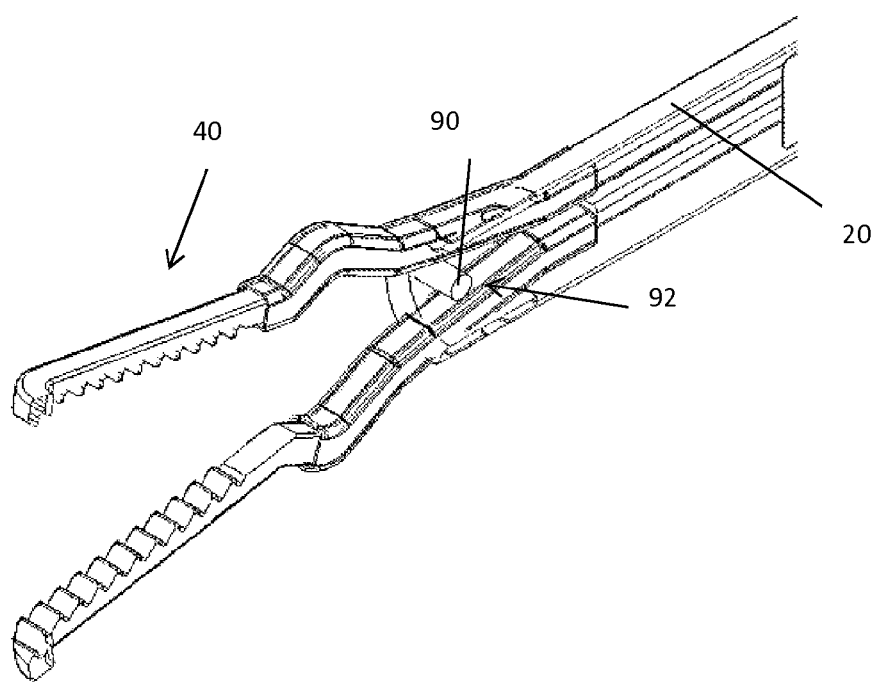
FIG. 15 illustrates a cross-sectional view of laparoscopic forceps of FIG. 16.
Figure 16:
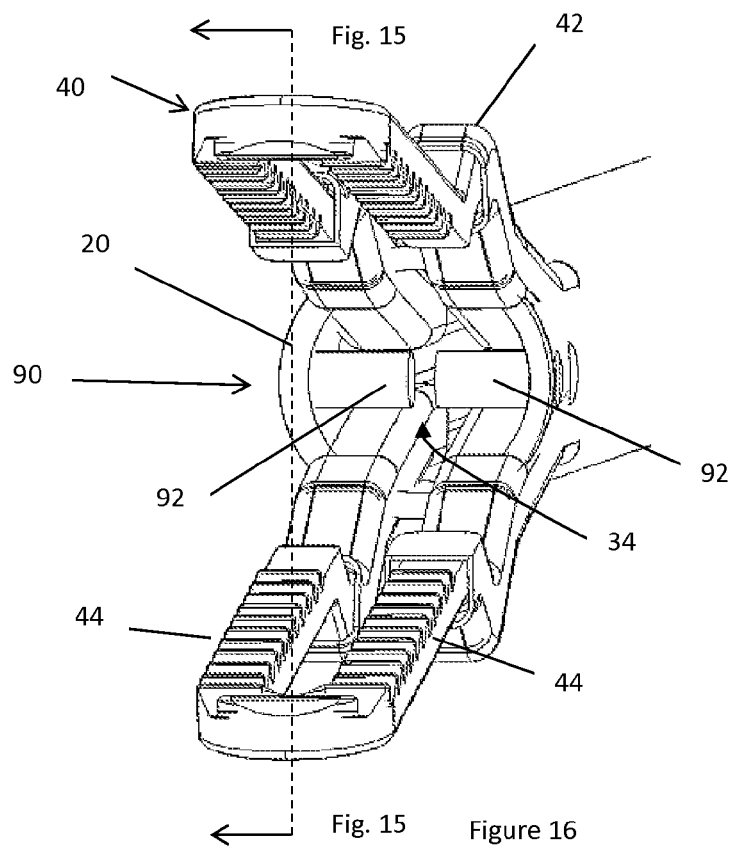
FIG. 16 illustrates a perspective view of a distal end of the laparoscopic forceps.

FIG. 15 illustrates a cross-sectional view of FIG. 16 cut along lines 15-15. The jaws 40 extend from a tubular member 20. The spacing member 90, which is configured as a pin 92 extends directly from the tubular member 20.

FIG. 16 illustrates a perspective view of the jaws 40 in an open position. The jaws 40 include an arcuate segment 42 on each leg 44 of the jaw 40. The tubular member 20 is moved into a retracted position and moves the spacing member 90 towards a proximal end so that as the spacing member 90 is moved toward the proximal end the legs 44 of the jaw 40 are moved apart and the jaws 40 are opened. The spacing member 90 is a pair of pins 92 that extend from the tubular member 20 and have a blade recess 34 therebetween.

Figure 17A:
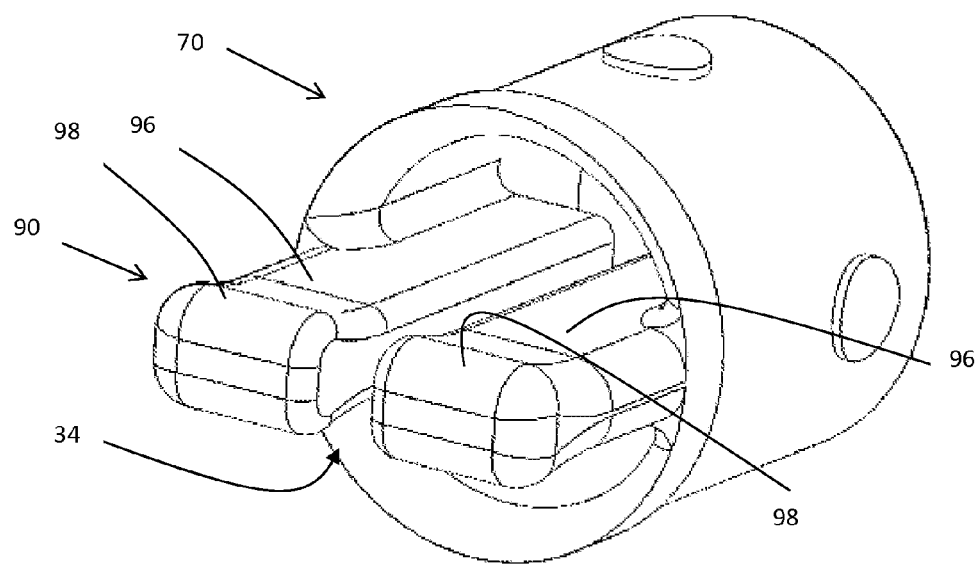
FIG. 17A illustrates a perspective view of a camming shaft.

FIG. 17A illustrates a perspective view of a camming shaft 70. The camming shaft 70 includes a pair of spacing members 90 with a blade recess 34 extending between the spacing members 90. Each of the spacing members include a bar 96 and a bulbous portion 98 that has an expanded thickness relative to the side of the bar 96.

Figure 17B:
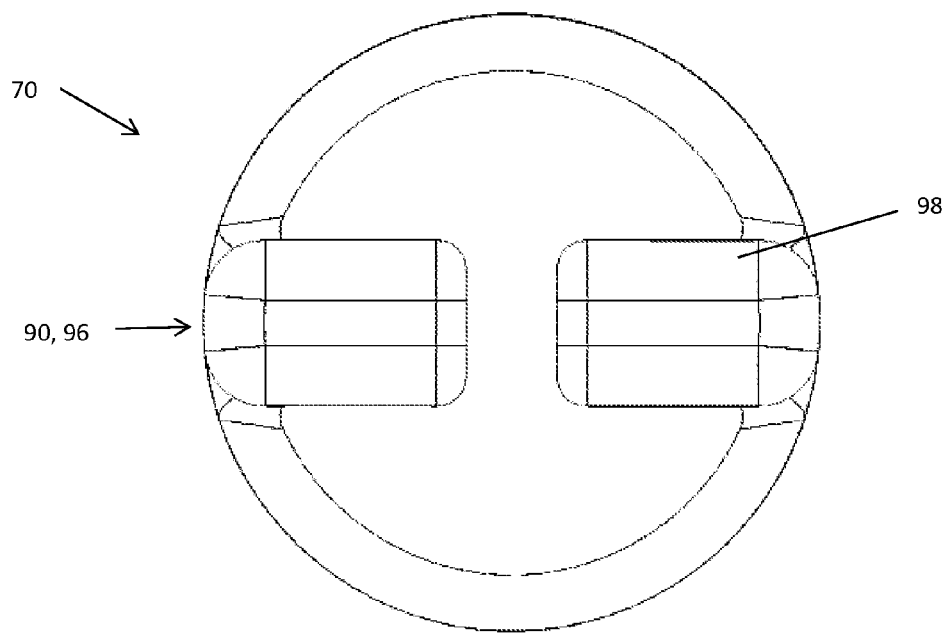
FIG. 17B illustrates an end of the camming shaft of FIG. 17A.

FIG. 17B illustrates a front view of the camming shaft 70 with the spacing members 90 extending therefrom and a blade recess 34 located therebetween. The bulbous portion 98 is shown covering the bar 96 so that the bar 96 is not shown.

Figure 18:
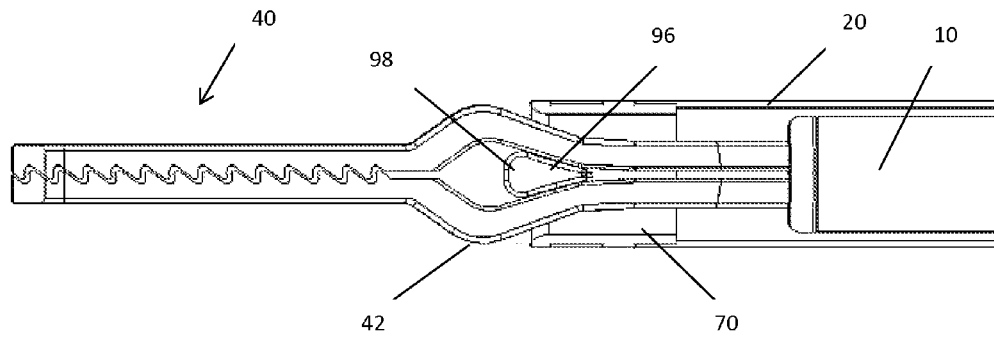
FIG. 18 illustrates a cross-sectional view of an example of jaws of laparoscopic forceps in a closed position.

FIG. 18 illustrates a cross-sectional view of the forceps 2. The jaws 40 closed around the spacing member 90. The spacing member 90 includes a bar 96 and a bulbous portion 98 that mirror the shape of the arcuate portion 42. The arcuate portion 42 is being contacted by the tubular member 20 so that the jaws 40 are closed. The end of the tubular member 20 includes a camming shaft 70 that assists in guiding the jaws 40 within the tubular member 20. A blade 10 is shown within the tubular member 20 and extending along the legs 44.

Figure 19:
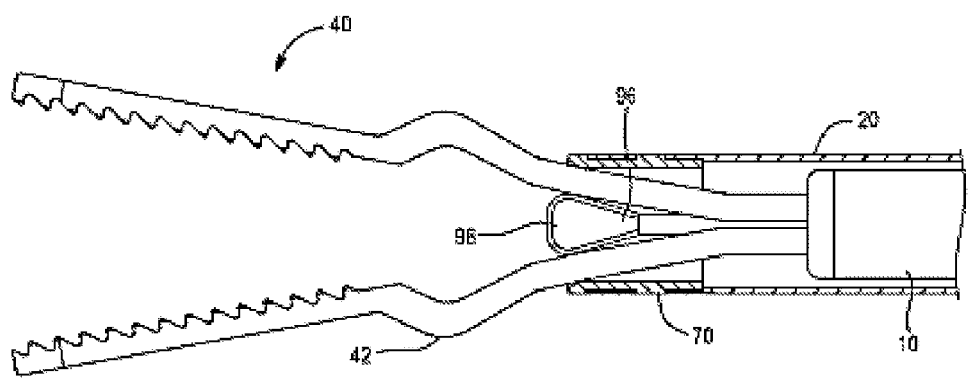
FIG. 19 illustrates a cross-sectional view of an example of open jaws of laparoscopic forceps in an open position.

FIG. 19 illustrates a cross-sectional view of the forceps 2 of FIG. 18 in an open state.

Figure 20:
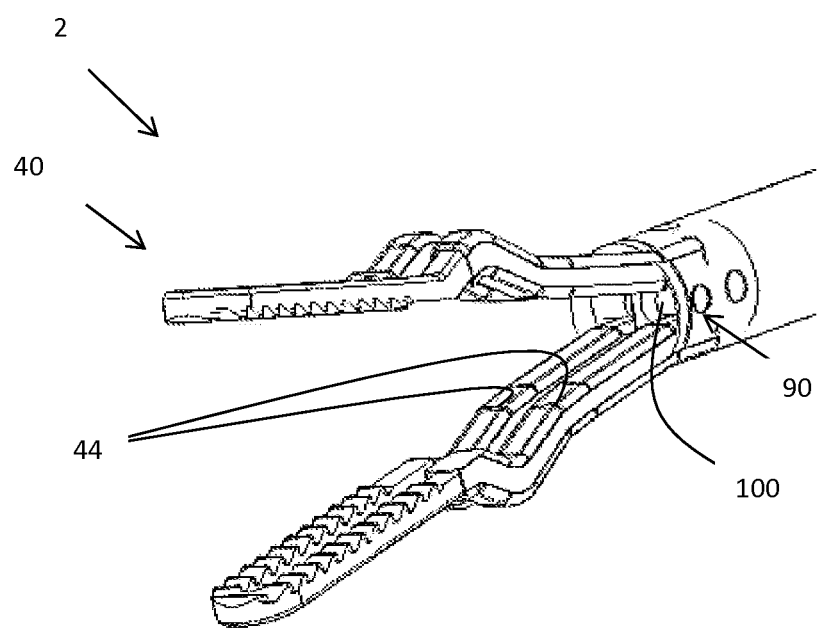
FIG. 20 illustrates a perspective view of a distal end of laparoscopic forceps.

FIG. 20 illustrates a perspective view of the forceps 2 with the jaws 40 in an open state. As illustrated, the tubular member 20 is in a retracted position so that the spacing member is moved backwards along the legs 44 so that the mushroom pin 100 of the spacing member 90 separates the legs 44 and the jaws 40.

Figure 21:
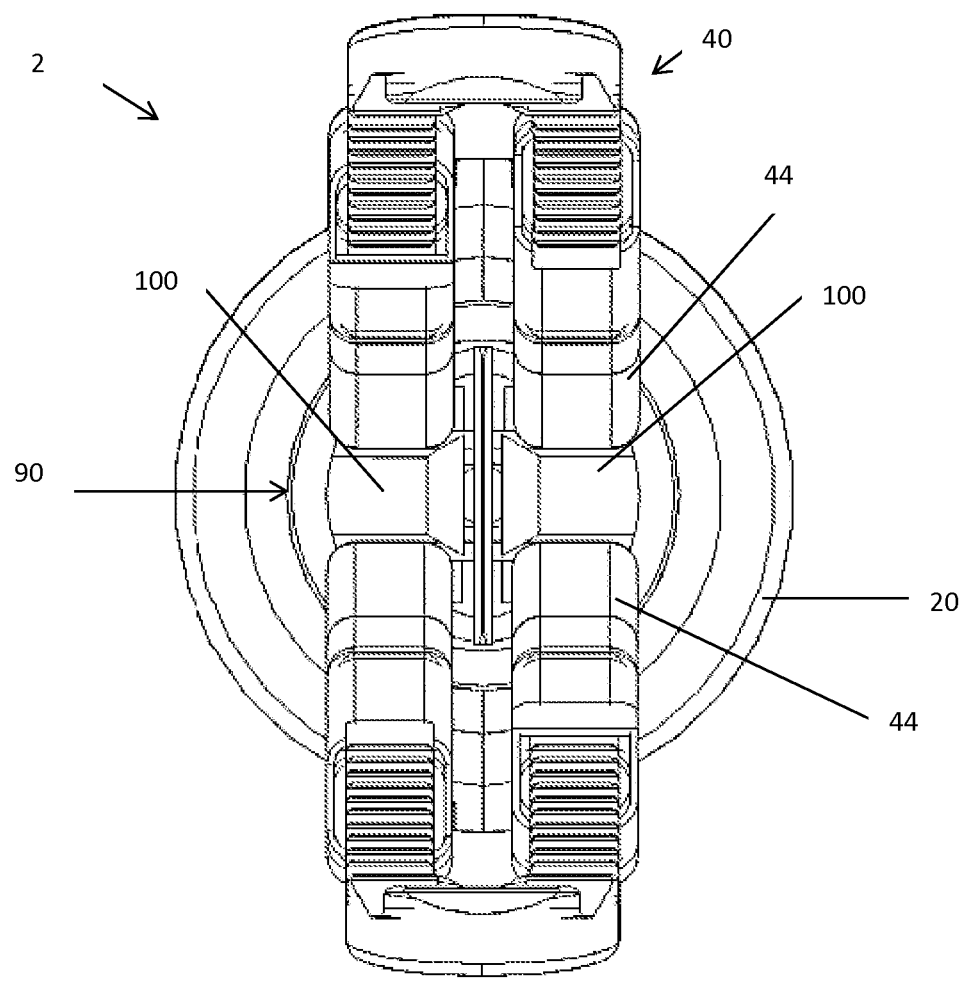
FIG. 21 illustrates an end view of the laparoscopic forceps of FIG. 20.

FIG. 21 illustrates an end view of the forceps 2 of FIG. 20. The jaws 40 as shown extend out of a tubular member 20. The pair of opposing jaws 40 are separated by a pair of spacing members 90 that include a mushroom pin 100 that forces the jaws 44 apart when the tubular member 20 is retracted so that the jaws 44 from an open position.

Figure 22:
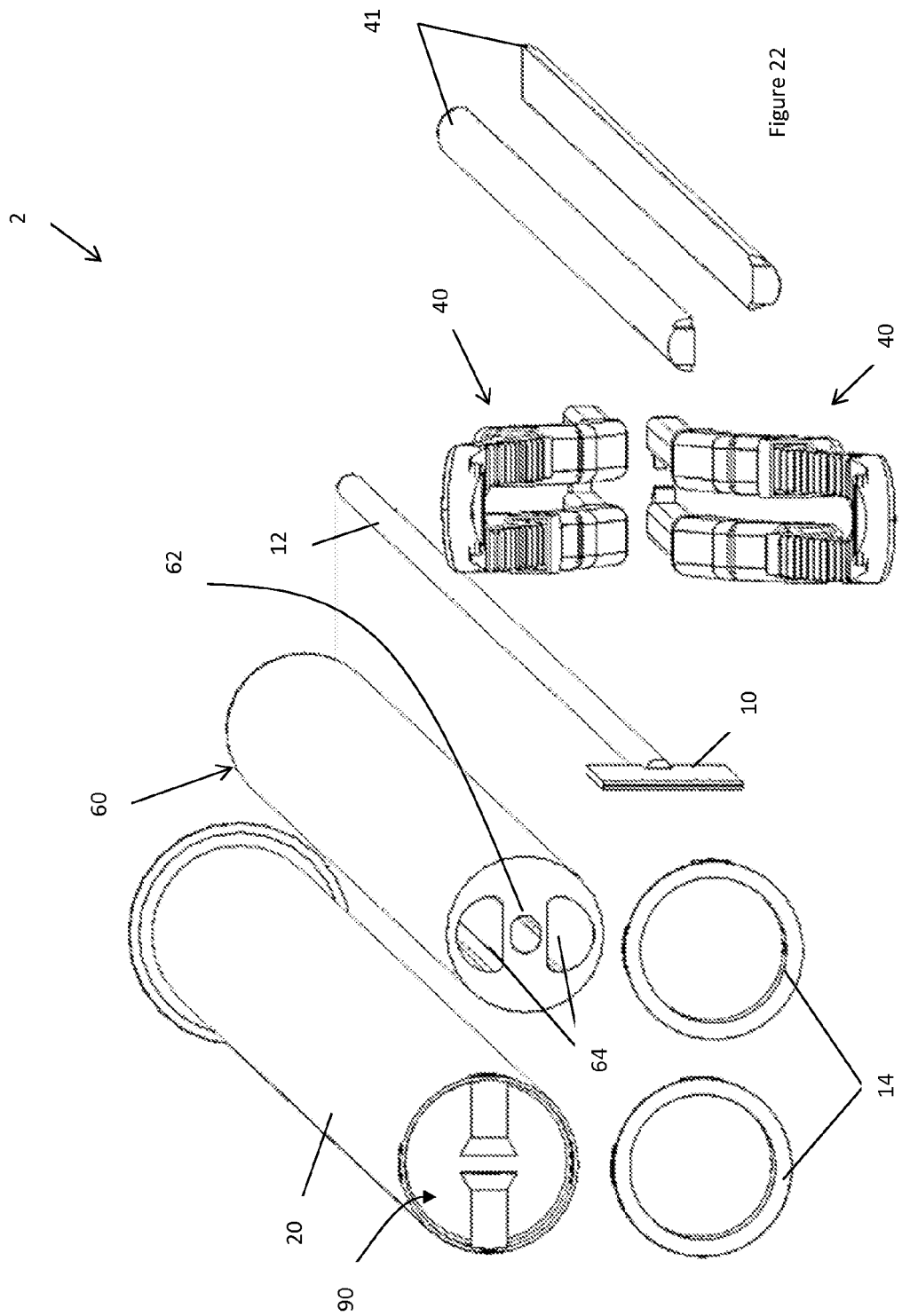
FIG. 22 illustrates an exploded view of laparoscopic forceps.

FIG. 22 illustrates an exploded view of the forceps 2 of FIG. 20. The forceps include a tubular member 20 including a pair of opposing spacing members 90. The tubular member 20 includes a guide 60 with a pair of jaw shaft guides 64 and a blade shaft guide 62 extending therethrough so that the jaw shafts 41 and the blade shaft 12 are guided through the tubular member 20 during movement of the opposing jaws 40. A pair of spacers 14 are located between the tubular member 20 and the guide 60. The forceps 2 include a blade 10 and a blade shaft 12 that are guided through and along the blade shaft guide 62. The jaws 40 are each connected to a jaw shaft 41 that extends through a pair of jaw shaft guides 64.

Figure 23:
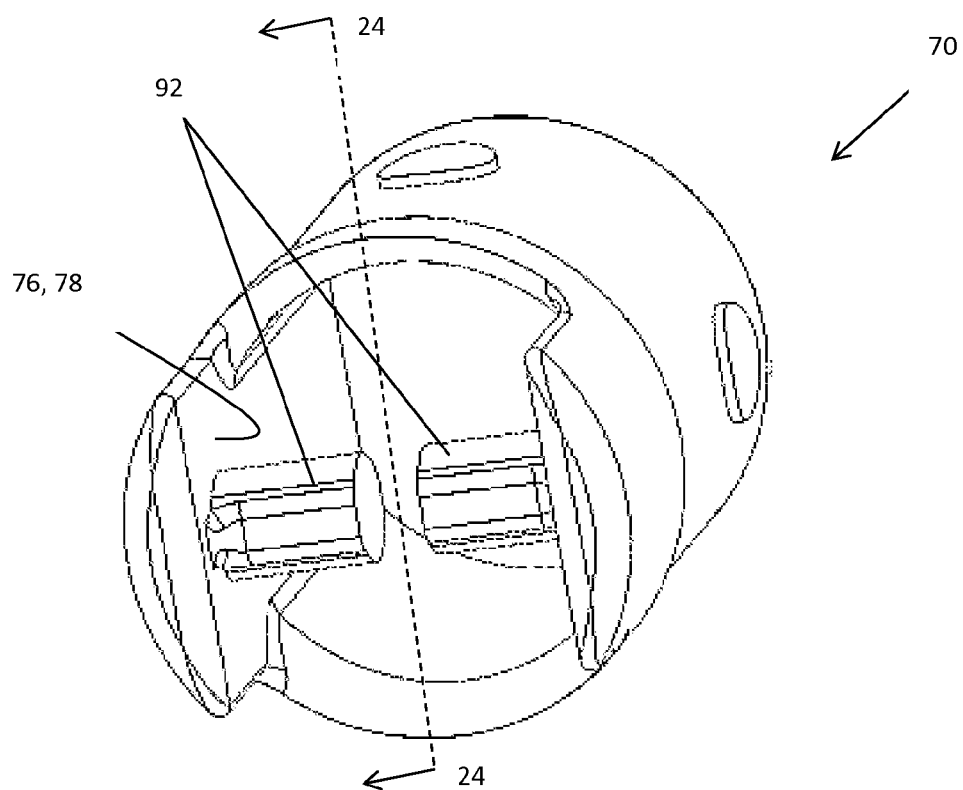
FIG. 23 illustrates a perspective view of a camming shaft and/or end of a tubular member.

FIG. 23 illustrates a perspective view of a camming shaft 70. The camming shaft 70 includes a pair of spaced apart pins 92 that extend from a sidewall 76 that include padding 78.

Figure 24:
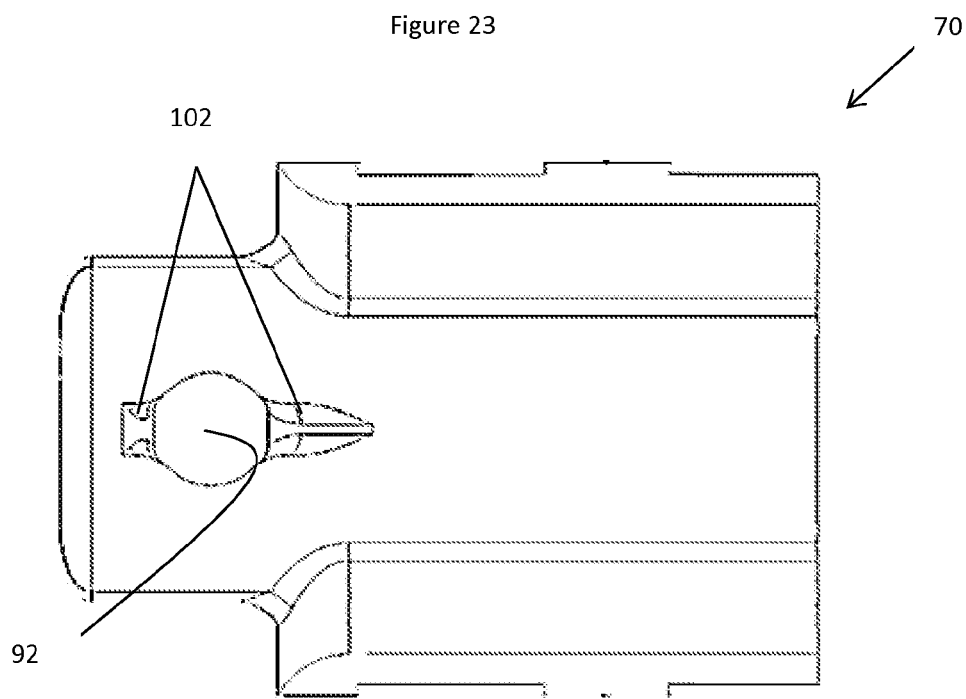
FIG. 24 illustrates a cross-sectional view of a camming shaft and/or tubular member of FIG. 23.

FIG. 24 illustrates a cross-sectional view of the camming shaft 70 of FIG. 23 cut along line 24-24. The camming shaft 70 includes a pin 92 including tapered portions 102 for guiding the legs (not shown).

Figure 25A:
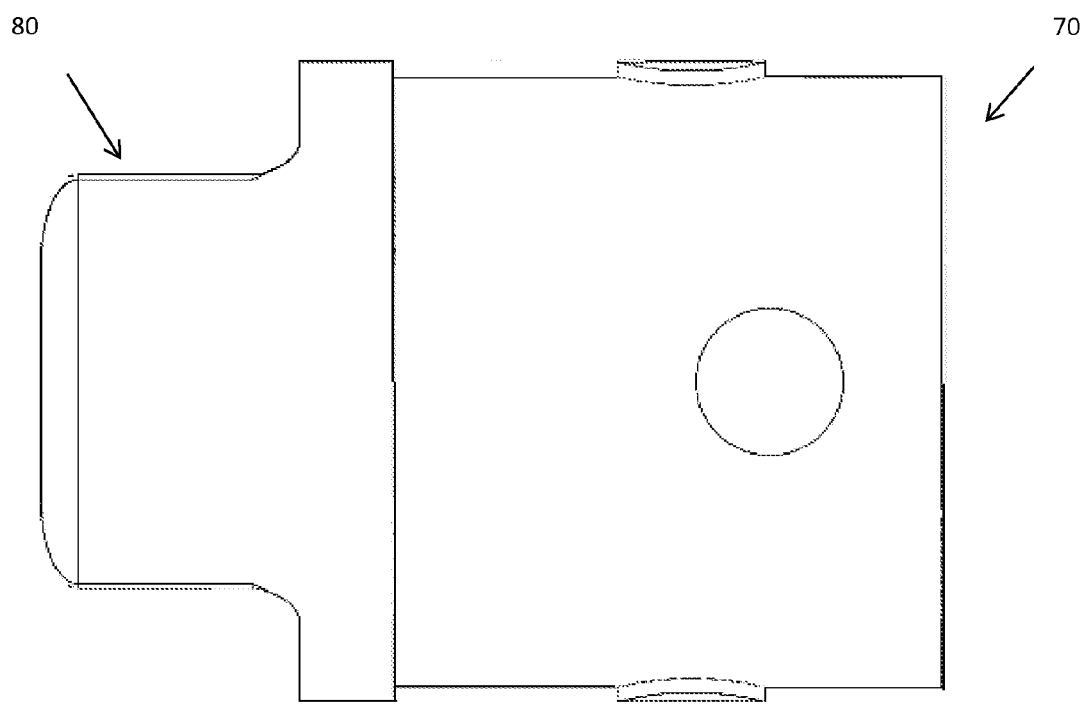
FIG. 25A illustrates a side view of a tubular member and/or a camming shaft.

FIG. 25A illustrates a side view of a camming shaft 70. The camming shaft 70 includes an ear 80 that has a generally rectangular shape.

Figure 25B:
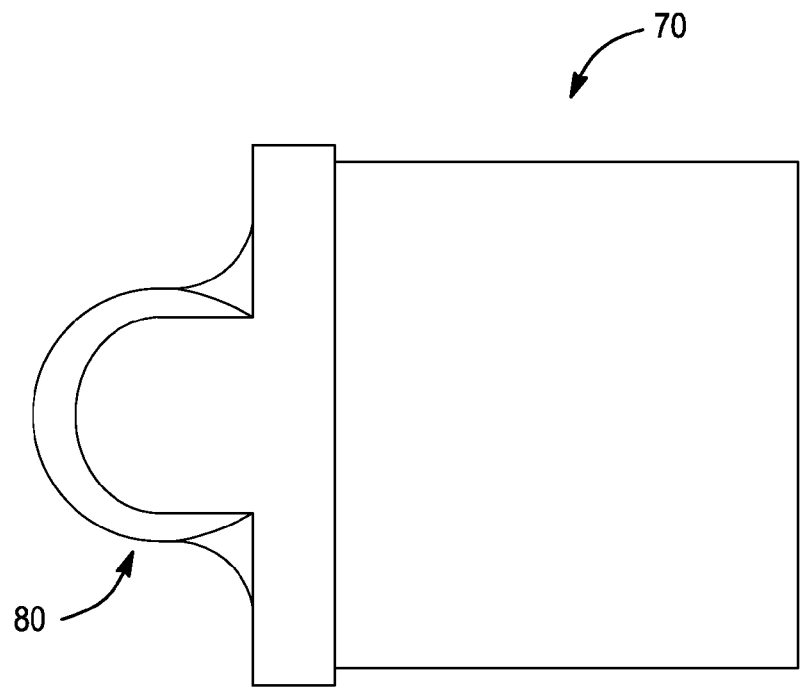
FIG. 25B illustrates a side view of a tubular member and/or a camming shaft.

FIG. 25B illustrates a side view of a camming shaft 70 with an ear 80 that has a generally circular shape.

Figure 26:
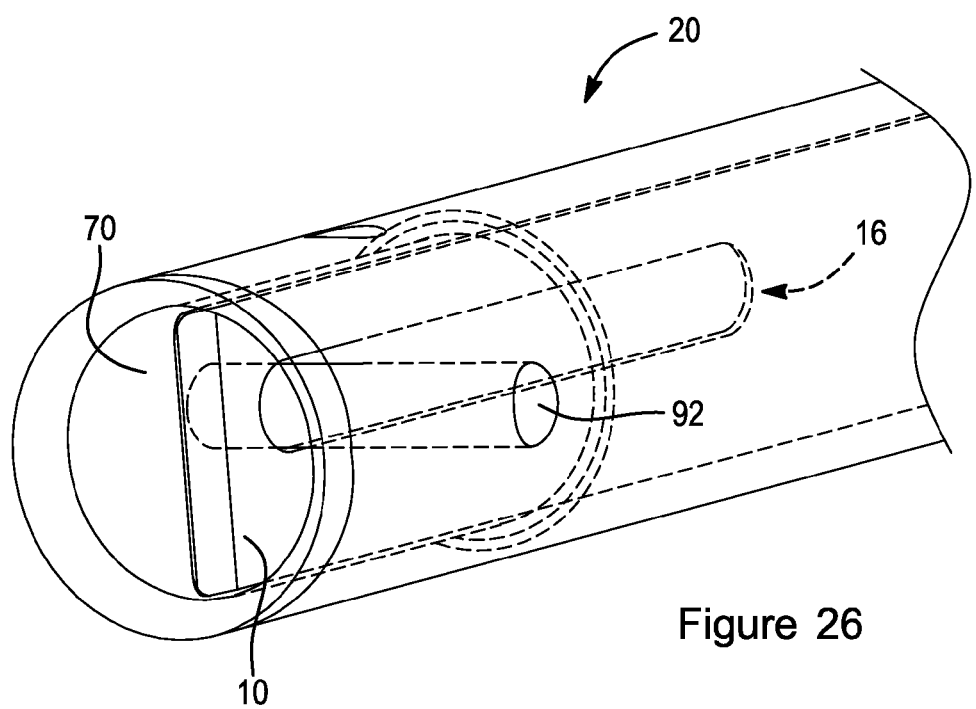
FIG. 26 illustrates a perspective view of a camming shaft located within a tubular member.

FIG. 26 illustrates a tubular member 20 with a camming shaft 70 in the opening of the tubular member 20 and a pin 92 extending across the opening of the tubular member 20 and the camming shaft 70. A blade 10 is shown with a pin recess 16 so that the pin 92 extends through the blade 12 and the blade is longitudinally movable.

Figure 27:
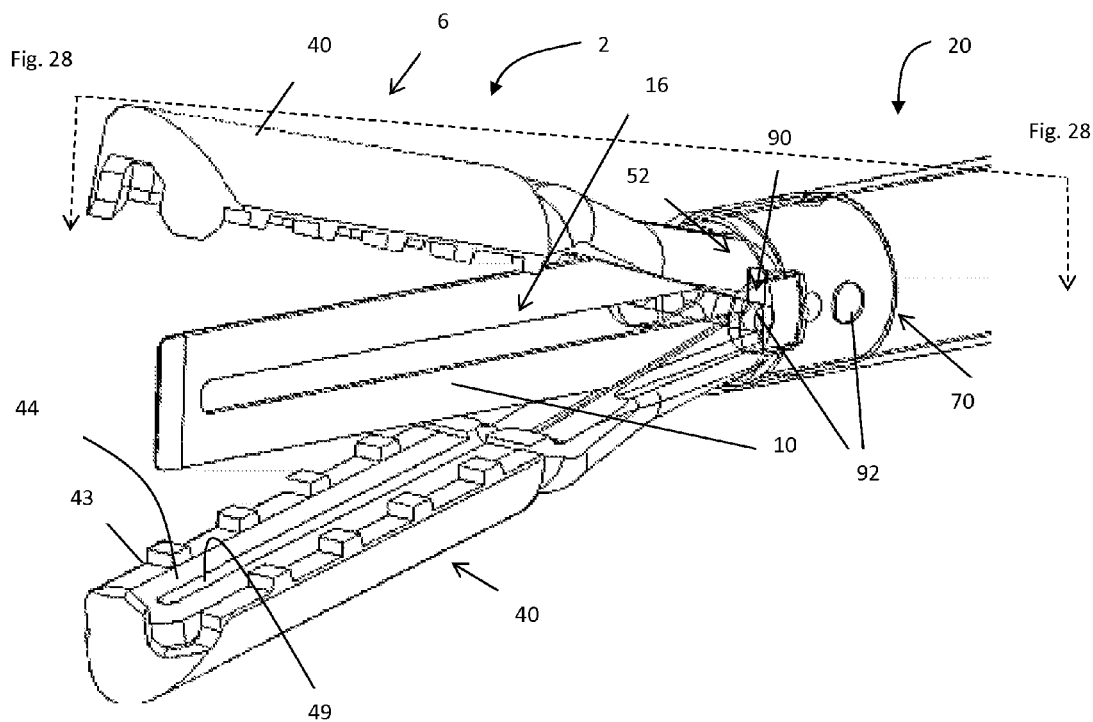
FIG. 27 illustrates a perspective view of laparoscopic forceps that include pivoting jaws.

FIG. 27 illustrates a perspective view of an end of a distal end 6 of laparoscopic forceps 2. The distal end includes a tubular member 20 connected to a pair of opposing jaws 40. The tubular member includes a spacing member 90 that is configured as a pin 92. The tubular member also includes a camming shaft 70 that includes a pin 92 extending there through. The pin 92 of the camming shaft 70 is connected to pivot joints 52 of the jaws 40. The jaws 40 include legs 44 that are covered with a protective cover 43 and the legs 44 have a blade track 49 extending between the legs 44. When the jaws 40 are closed the blade 10 extends through the blade track 49 to perform a cutting function. The blade 10 includes a pin recess 16 that the pins 92 extend through so that the blade 10 is axially movable.

Figure 28:
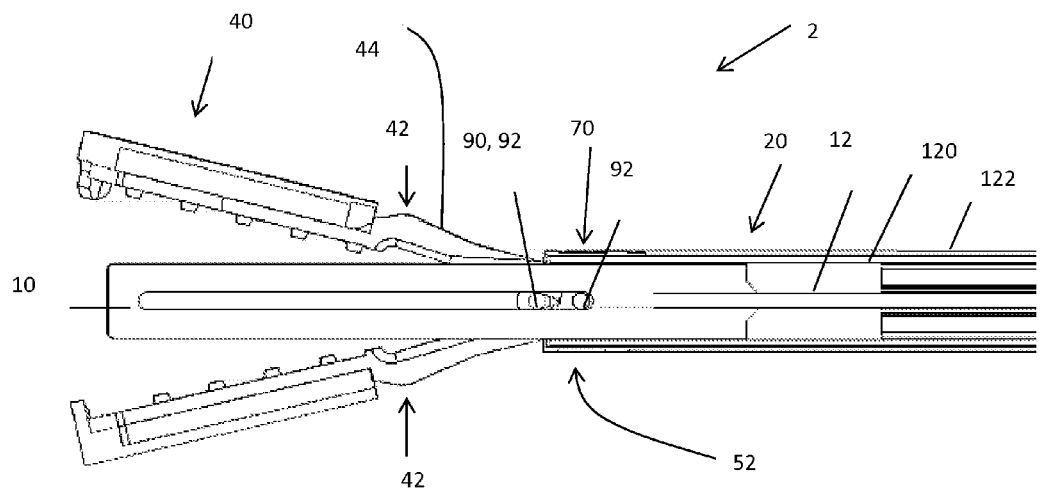
FIG. 28 illustrates a cross-sectional view of the laparoscopic forceps of FIG. 27.

FIG. 28 illustrates a cross-sectional view of the laparoscopic forceps 2 of FIG. 27 cut along lines 28-28. The laparoscopic forceps 2 include a tubular member 20. The tubular member 20 has an inner tube 120 and an outer tube 122 that extends along a portion of the inner tube 120 and a blade shaft 12, and the blade 10 extends through the tubular member 20 and the inner tube 120. The inner tube 120 includes a camming shaft 70 that has a pin 92 extending across the camming shaft 70. The pin 92 is connected to a pivot joint 52 of the jaws 40. A spacing member 90 configured as a pin 92 is located in front of the pin 92 of the camming shaft 70. The spacing member 90 separates the jaws 40 when the jaws are moved distally or the tubular member 20 is moved proximally. The jaws 40 include an arcuate section 42 in the legs 44 that assists in closing the jaws 40 when the arcuate sections 42 contact the tubular member 20. A blade 10 is located between the jaws 40.

Figure 29:
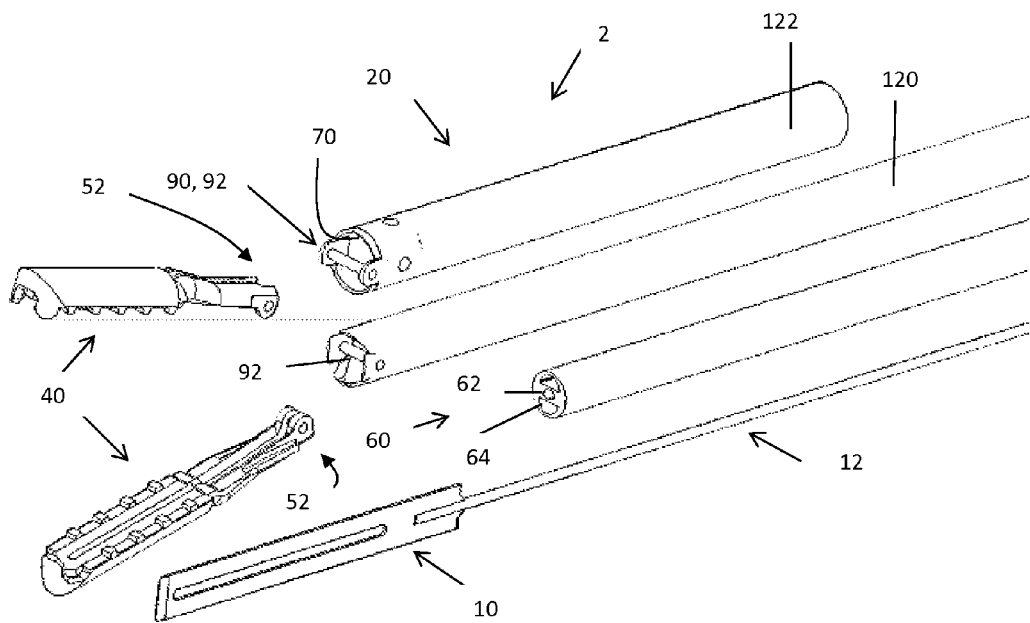
FIG. 29 illustrates an exploded view of laparoscopic forceps including pivoting jaws.

FIG. 29 illustrates an exploded view of laparoscopic forceps 2. The laparoscopic forceps 2 include a tubular member 20 that includes an outer tube 122 that houses an inner tube 120 and a blade shaft 12. The tubular member 20 includes a camming shaft 70 including a spacing member 90 that is configured as a pin 92. The spacing member 90 is located distal of a pin 92 of the inner tube 120. A guide 60 is located within the inner tube 120. The guide includes blade shaft guides 62 and a jaw shaft guide 64 that receives the blade shaft 12. The blade shaft 12 is connected to a blade 10 that extends between a pair of opposing jaws 40. The pair of opposing jaws 40 each include a pivot joint 52 that is connected to a pin 92 of the inner tube 120.

Figure 30:
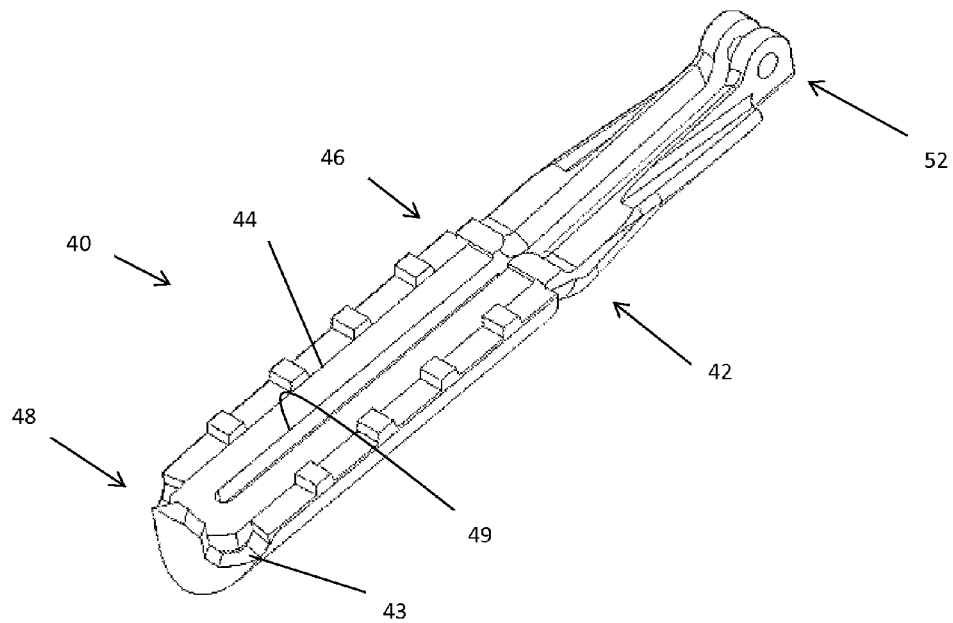
FIG. 30 illustrates a close-up view of a pivoting jaw of the teachings herein.

FIG. 30 illustrates a jaw 40. The jaw 40 includes legs 44 having an arcuate section 42 that assist in closing the jaws 40. The legs 44 include a blade track 49 extending therebetween. The jaws 40 include a protective cover 43 that extends from heel 46 to the front 48 of the jaws 40. A pivot joint 52 is located at a proximate end of the jaw 40 so that the jaw 40 can pivot from an open position to a closed position.

Figure 31:
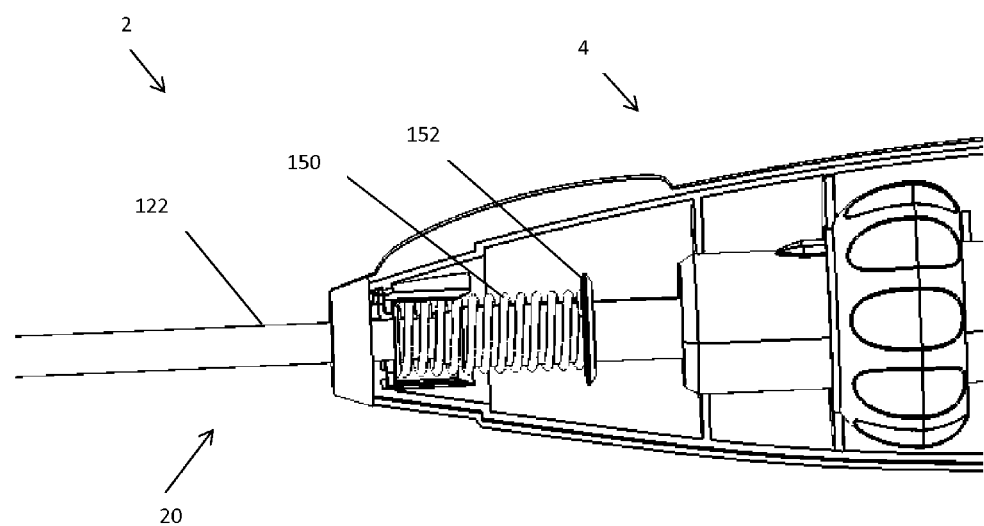
FIG. 31 illustrates a side view of one example of a handpiece with a cover removed, the handpiece including a biasing member.

FIG. 31 illustrates a side view of a handpiece 4 of laparoscopic forceps 2 with a cover removed. A tubular member 20 is extending from the handpiece 4. The tubular member is in communication with a biasing member 150 and locking member 152 that move the outer tube 122 relative to the inner tube 120 (not shown).

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A laparoscopic forceps comprising:
   a) a handpiece;
   b) a biasing member;
   c) a tubular member including:
      i. an outer tube, and
      ii. an inner tube, wherein the outer tube and inner tube are configured for relative axial motion when acted upon by the biasing member; and
   d) two or more jaws that extend out of the tubular member and the two or more jaws pivot on a common axis that is anchored to the inner tube, wherein each of the two or more jaws has an arcuate section;
   e) a blade and the blade includes a pin recess that receives a portion of a pin so that the blade is movable along a longitudinal axis of the tubular member;
   wherein the outer tube, during actuation of the biasing member, overruns the two or more jaws so that the two or more jaws are moved towards each other; wherein one or more spacing members extend across a distal opening of the tubular member and between the two or more jaws; and
   wherein the two or more jaws are closable by the relative movement of the tubular member and the two or more jaws towards each other so that the tubular member advances over the arcuate section of the two or more jaws, and the two or more are openable by the relative movement of the tubular member and the two or more jaws away from each other so that the one or more spacing members extend between the two or more jaws so that the two or more jaws are moved apart.

2. The laparoscopic forceps of claim 1, wherein the common axis is a pin that connects each of the two or more jaws to the tubular member.

3. The laparoscopic forceps of claim 1, wherein a spacing member is connected to the outer tube so that the spacing member drives the two or more jaws apart.

4. The laparoscopic forceps of claim 1, wherein the handpiece includes a distal end portion.

5. The laparoscopic forceps of claim 4, wherein the tubular member protrudes from the distal end portion of the handpiece and the tubular member has a distal end and a distal opening.

6. The laparoscopic forceps of claim 5, wherein the two or more jaws have legs that are disposed within the tubular member and partially protrude from the distal opening in the distal end of the tubular member and the two or more jaws and the tubular member are movable relative to each other in a direction parallel to the longitudinal axis of the tubular member.

7. The laparoscopic forceps of claim 6, wherein each of the two or more jaws has an operable mechanism for creating relative motion between the two or more jaws and the tubular member along a direction parallel to the longitudinal axis of the tubular member.

8. The laparoscopic forceps of claim 7, wherein the laparoscopic forceps include a camming shaft that is located in the distal end of the tubular member.

9. The laparoscopic forceps of claim 8, wherein the one or more spacing members are a pair of opposing pins that include a blade recess therebetween, one continuous spacing member that extends across the distal opening of the tubular member, or both.

10. The laparoscopic forceps of claim 9, wherein the one or more spacing members include a generally mushroom shape and/or are crimped material of the tubular member, the camming shaft, or both.

11. The laparoscopic forceps of claim 10, wherein the one or more spacing members are one or more bars that extend out of the distal opening of the tubular member along the longitudinal axis of the tubular member.

12. The laparoscopic forceps of claim 11, wherein the one or more bars each include a bulbous portion at an end that increases a size of each of the one or more bars so that when the bulbous portion contacts the two or more jaws, the legs of the two or more jaws, or both as the two or more jaws are moved apart.

13. The laparoscopic forceps of claim 12, wherein the laparoscopic forceps include a blade and the blade has a pin recess that extends along the longitudinal axis of the tubular member, and the one or more spacing members extend through the pin recess so that the blade is extendable and retractable.

14. The laparoscopic forceps of claim 13, wherein the jaws include a pivot joint that the jaws rotate about to open and close.

15. The laparoscopic forceps of claim 14, wherein the inner tube extends within all or a portion of the outer tube.

16. The laparoscopic forceps of claim 15, wherein a spacing members maintains the jaws in an open state.

17. The laparoscopic forceps of claim 1, wherein the tubular member includes a blade recess.

18. The laparoscopic forceps of claim 1, wherein the tubular member includes internal flat portions.

19. The laparoscopic forceps of claim 1, wherein the tubular member includes a one or more pocket surfaces and the one or more pocket surfaces are complementary in shape to the legs of the two or more jaws.

* * * * *